US009284286B2

(12) United States Patent
Lucas et al.

(10) Patent No.: US 9,284,286 B2
(45) Date of Patent: Mar. 15, 2016

(54) SPECIFIC CARBOXAMIDES AS KCNQ2/3 MODULATORS

(71) Applicant: GRÜNENTHAL GMBH, Aachen (DE)

(72) Inventors: Simon Lucas, Wolfsgraben (AT); Sven Kühnert, Düren (DE); Gregor Bahrenberg, Monschau-Konzen (DE); Wolfgang Schröder, Aachen (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/091,373

(22) Filed: Nov. 27, 2013

(65) Prior Publication Data
US 2014/0148468 A1  May 29, 2014

Related U.S. Application Data

(60) Provisional application No. 61/730,529, filed on Nov. 28, 2012.

(30) Foreign Application Priority Data

Nov. 28, 2012 (EP) .................................... 12007992

(51) Int. Cl.
| C07D 277/56 | (2006.01) |
| C07C 323/62 | (2006.01) |
| C07D 495/04 | (2006.01) |
| C07D 471/04 | (2006.01) |
| C07D 213/82 | (2006.01) |
| C07D 239/38 | (2006.01) |
| A61K 31/44 | (2006.01) |
| C07D 237/24 | (2006.01) |
| A61K 31/4965 | (2006.01) |
| C07D 241/24 | (2006.01) |
| A61K 31/166 | (2006.01) |
| A61K 31/505 | (2006.01) |
| A61K 31/426 | (2006.01) |
| A61K 31/4436 | (2006.01) |
| A61K 31/50 | (2006.01) |
| C07D 213/81 | (2006.01) |
| C07D 409/12 | (2006.01) |

(52) U.S. Cl.
CPC ............ *C07D 277/56* (2013.01); *A61K 31/166* (2013.01); *A61K 31/426* (2013.01); *A61K 31/44* (2013.01); *A61K 31/4436* (2013.01); *A61K 31/4965* (2013.01); *A61K 31/50* (2013.01); *A61K 31/505* (2013.01); *C07C 323/62* (2013.01); *C07D 213/81* (2013.01); *C07D 213/82* (2013.01); *C07D 237/24* (2013.01); *C07D 239/38* (2013.01); *C07D 241/24* (2013.01); *C07D 409/12* (2013.01); *C07D 471/04* (2013.01); *C07D 495/04* (2013.01)

(58) Field of Classification Search
CPC .. C07D 471/04; C07D 277/56; C07D 495/04; C07D 213/82; C07D 239/38; C07D 237/24; C07D 241/24; C07D 213/81; C07D 409/12; C07C 323/62; A61K 31/44; A61K 31/4965; A61K 31/166; A61K 31/505; A61K 31/4436; A61K 31/50; A61K 31/40
USPC ............ 549/59; 514/618, 291, 346, 247, 369, 514/336, 406, 319, 269; 548/188; 544/239; 564/162; 546/280
See application file for complete search history.

(56) References Cited

U.S. PATENT DOCUMENTS

| 7,625,900 | B2 | 12/2009 | Merla et al. |
| 7,879,858 | B2 | 2/2011 | Merla et al. |
| 8,017,772 | B2 | 9/2011 | Merla et al. |
| 8,084,470 | B2 | 12/2011 | Merla et al. |
| 8,133,907 | B2 | 3/2012 | Blaszczak et al. |
| 8,178,684 | B2 | 5/2012 | Kuehnert et al. |
| 8,399,673 | B2 | 3/2013 | Kuehnert et al. |
| 8,445,512 | B2 | 5/2013 | Kuhnert et al. |
| 8,470,852 | B2 | 6/2013 | Kuehnert et al. |
| 8,552,200 | B2 | 10/2013 | Kuehnert et al. |
| 8,586,755 | B2 | 11/2013 | Kuehnert et al. |
| 2002/0128277 | A1 | 9/2002 | Dworetzky et al. |
| 2002/0183335 | A1 | 12/2002 | Hewawasam et al. |
| 2005/0250818 | A1 | 11/2005 | Koike et al. |
| 2008/0167315 | A1 | 7/2008 | Merla et al. |
| 2008/0214616 | A1 | 9/2008 | Blaszczak et al. |

(Continued)

FOREIGN PATENT DOCUMENTS

| EP | 1 219 609 | 7/2002 |
| WO | 94 15608 | 7/1994 |
| WO | WO 9415608 A1 * | 7/1994 |
| WO | 02 066036 | 8/2002 |
| WO | 2005 105733 | 11/2005 |
| WO | 2005 105733 A1 | 11/2005 |
| WO | 2006 058905 | 6/2006 |
| WO | 2007 015767 | 2/2007 |
| WO | 2007 015767 A1 | 2/2007 |
| WO | 2007 138110 | 12/2007 |

(Continued)

OTHER PUBLICATIONS

Chiang, C., "Formulation development of an oral dosage form for an hiv protease inhibitor, AG1284." International journal of pharmaceutics 117.2 (1995): 197-207.*

(Continued)

*Primary Examiner* — Samantha Shterengarts
*Assistant Examiner* — Matt Mauro
(74) *Attorney, Agent, or Firm* — Norris McLaughlin & Marcus, P.A.

(57) ABSTRACT

The invention relates to specific carboxamides, to processes for their preparation, to medicaments comprising these compounds and to the use of these compounds in the preparation of medicaments.

16 Claims, No Drawings

(56) References Cited

U.S. PATENT DOCUMENTS

| | | |
|---|---|---|
| 2009/0076086 A1 | 3/2009 | Merla et al. |
| 2009/0258880 A1 | 10/2009 | Merla et al. |
| 2010/0004252 A1 | 1/2010 | Merla et al. |
| 2010/0022589 A1 | 1/2010 | McCoull et al. |
| 2010/0105722 A1 | 4/2010 | Kuehnert et al. |
| 2010/0234372 A1 | 9/2010 | Kuehnert et al. |
| 2010/0234429 A1 | 9/2010 | Kuehnert et al. |
| 2012/0053204 A1 | 3/2012 | Kuehnert et al. |
| 2012/0053205 A1 | 3/2012 | Kuehnert et al. |
| 2012/0101079 A1 | 4/2012 | Kuehnert et al. |
| 2012/0184550 A1 | 7/2012 | Kuehnert et al. |
| 2012/0220627 A1 | 8/2012 | Kuehnert et al. |
| 2012/0252841 A1 | 10/2012 | Kuehnert et al. |
| 2012/0258947 A1 | 10/2012 | Kühnert et al. |

FOREIGN PATENT DOCUMENTS

| | | |
|---|---|---|
| WO | 2008 012532 | 1/2008 |
| WO | 2008 012532 A2 | 1/2008 |
| WO | 2008 046582 | 4/2008 |
| WO | 2009 036938 | 3/2009 |
| WO | 2009 036938 A1 | 3/2009 |
| WO | 2010 046108 | 4/2010 |
| WO | 2010/097410 A1 | 9/2010 |
| WO | 2010 102809 | 9/2010 |
| WO | 2010 102809 A1 | 9/2010 |
| WO | 2010 102811 | 9/2010 |
| WO | 2012 025236 | 3/2012 |
| WO | 2012 025237 | 3/2012 |
| WO | 2012 025238 | 3/2012 |
| WO | 2012 052167 | 4/2012 |

OTHER PUBLICATIONS

Wermuth, C.G., "Molecular variations based on isosteric replacements." The Practice of Medicinal Chemistry 2 (1996).*
Ravin Louis J., "Preformulation", "Remington's Pharmaceutical Sciences", ed. A.R. Gennaro, 17th ed., Mack Publishing Company, Easton, Pa. (1985), Chapter 76, p. 1409-1423.
DiSanto, Anthony R., "Bioavialiblity and Bioequivalency Testing", "Remington's Pharmaceutical Sciences", ed. A.R. Gennaro, 17th ed., Mack Publishing Company, Easton, Pa. (1985), Chapter 77, p. 1424-1431.
Knevel, Adelbert M., "Separation", "Remington's Pharmaceutical Sciences", ed. A.R. Gennaro, 17th ed., Mack Publishing Company, Easton, Pa. (1985), Chapter 78, p. 1432-1442.
Phillips, G Briggs et al., "Sterilization", "Remington's Pharmaceutical Sciences", ed. A.R. Gennaro, 17th ed., Mack Publishing Company, Easton, Pa. (1985), Chapter 79, p. 1443-1454.
Siegel, Frederick P., "Tonicity, Osmoticity, Osmolality, and Osmolarity", "Remington's Pharmaceutical Sciences", ed. A.R. Gennaro, 17th ed., Mack Publishing Company, Easton, Pa. (1985), Chapter 80, p. 1455-1472.
Giles, Robert L. et al., "Plastic Packaging Materials", "Remington's Pharmaceutical Sciences", ed. A.R. Gennaro, 17th ed., Mack Publishing Company, Easton, Pa. (1985), Chapter 81, p. 1473-1477.
Lintner, Carl J., "Stability of Pharmaceutical Products", "Remington's Pharmaceutical Sciences", ed. A.R. Gennaro, 17th ed., Mack Publishing Company, Easton, Pa. (1985), Chapter 82, p. 1478-1486.
Erskine, Clyde R., "Quality Assurance and Control", "Remington's Pharmaceutical Sciences", ed. A.R. Gennaro, 17th ed., Mack Publishing Company, Easton, Pa. (1985), Chapter 83, p. 1487-1491.
Nairn, J G., "Sloutions, Emulsions, Suspensions and Extractives", "Remington's Pharmaceutical Sciences", ed. A.R. Gennaro, 17th ed., Mack Publishing Company, Easton, Pa. (1985), Chapter 84, p. 1492-1517.
Avis, Kenneth E., "Parenteral Preparations", "Remington's Pharmaceutical Sciences", ed. A.R. Gennaro, 17th ed., Mack Publishing Company, Easton, Pa. (1985), Chapter 85, p. 1518-1541.
Turco, Salvatore J. et al., "Intravenous Admixtures", "Remington's Pharmaceutical Sciences", ed. A.R. Gennaro, 17th ed., Mack Publishing Company, Easton, Pa. (1985), Chapter 86, p. 1542-1552.
Mullins, John, D., "Ophthalmic Preparations", "Remington's Pharmaceutical Sciences", ed. A.R. Gennaro, 17th ed., Mack Publishing Company, Easton, Pa. (1985), Chapter 87, p. 1553-1566.
Block, Lawrence H., "Medicated Applications", "Remington's Pharmaceutical Sciences", ed. A.R. Gennaro, 17th ed., Mack Publishing Company, Easton, Pa. (1985), Chapter 88, p. 1567-1584.
Ripple, Edward G., "Powders", "Remington's Pharmaceutical Sciences", ed. A.R. Gennaro, 17th ed., Mack Publishing Company, Easton, Pa. (1985), Chapter 89, p. 1585-1602.
King, Robert E. et al., "Oral Solid Dosage Forms", "Remington's Pharmaceutical Sciences", ed. A.R. Gennaro, 17th ed., Mack Publishing Company, Easton, Pa. (1985), Chapter 90, p. 1603-1632.
Porter, Stuart C., "Coating of Pharmaceutical Dosage Forms", "Remington's Pharmaceutical Sciences", ed. A.R. Gennaro, 17th ed., Mack Publishing Company, Easton, Pa. (1985), Chapter 91, p. 1633-1643.
Longer, Mark A., "Sustained-Release Drug Delivery Systems", "Remington's Pharmaceutical Sciences", ed. A.R. Gennaro, 17th ed., Mack Publishing Company, Easton, Pa. (1985), Chapter 92, p. 1644-1661.
Sciarra, John J., "Aerosols", "Remington's Pharmaceutical Sciences", ed. A.R. Gennaro, 17th ed., Mack Publishing Company, Easton, Pa. (1985), Chapter 93, p. 1662-1677.
D'Amour and Smith (J. Pharm. Exp. Ther. 72, 74 79 (1941).
D. Dubuisson et al., Pain 1977, 4, 161-174.
Zhou, Shao-Zhen et al, "Synthesis on new S,S-chelated Pd(I) complexes and their promoter effect on the hydrolytic cleavage of dipeptide", Chem. Abstr. Service, 1999.
European Search Report issued in corresponding application EP 12007990 dated Jan. 30, 2013.
European Search Report issued in corresponding application EP 12007991 dated Jun. 26, 2013.
European Search Report issued in corresponding application EP 12007992 dated Jul. 8, 2013.
Passmore et al; "KCNQ/M currents in sensory neurons: significance for pain therapy"; The Journal of Neuroscience, Aug. 6, 2003, 23(18), pp. 7227-7236.
Blackburn-Munro et al; "The anticonvulsant retigabine attenuates nociceptive behaviours in rat models of persistent and neuropathic pain": European Journal of Pharmacology 460 (2003) pp. 109-116.
Dost et al; "The anti-hyperalgesic activity of retigabine is mediated by KCNQ potassium channel activation" ; Naunyn-Schmiedeberg's Arch Pharmacol (2004) 369; pp. 382-390.
Gribkoff; "The therapeutic potential of neuronal KCNQ channel modulators"; Expert Opinion, Ther. Target, 2003; 7(6); pp. 737-748.
Korsgaard et al; "Anxiolytic effects of maxipost (BMS-204352) and retigabine via activation of neuronal Kv7 channels"; The Journal of Pharmacology and Experimental Therapeutics; Vo. 314, No. 1, pp. 282-292.
Wickenden et al; "KCNQ potassium channels: drug targets for the treatment of epilepsy and pain"; Expret Opinion, Monthly focus: Central & Peripheral Nervous Systems; Ashley Publications Ltd. 2004; pp. 457-469.
Gribkoff; Central & Peripheral Nervous Systems; "The therapeutic potential of neuronal Kv7 (KCNQ) channel modulators: an update"; Expert Opinion Ther. Targets 2008; 12(5); pp. 565-581.
Miceli et al; "Molecular pharmacology and therapeutic potential of neuronal Kv7-modulating drugs"; Current Opinion in Pharmacology 2008, 8, pp. 65-74.
Streng et al; "Urodynamic effects of K+ channel (KCNQ) opener retigabine in freely moving, conscious rats": The Journal of Urology, vol. 172, Nov. 2004, pp. 2054-2058.
Hansen et al; "The neuronal KCNQ channel opener retigabine inhibits locomotor activity and reduces forebrain excitatory responses to the psychostimulants cocaine, methylphenidate and phecyclidine"; European Journal of Pharmacology 570 (2007); pp. 77-88.
Dencker et al; "Effect of the new antiepileptic drug retrigabine in a rodent model of mania": Epilepsy & Behavior 12 (2008) pp. 49-53.

(56) References Cited

OTHER PUBLICATIONS

Richter et al; "Antidystonic effects of Kv7 (KCNQ) channel openers in the dt sz mutant, an animal model of primary paroxysmal dystonia": British Journal of Pharmacology (2006) 149, pp. 747-753.
Bennett et al; "A peripheral mononeuropathy in rat that produces disorders of pain sensation like those seen in man"; Pain, 33 (1988) pp. 87-107.
Kim et al; "An experimental model for peripheral neuropathy produced by segmental spinal nerve ligation in the rat" Pain, 50 (1992) pp. 355-363.
DeSarro et al; "Influence of retigabine on the anticonvulsant activity of some antiepileptic drugs against audiogenic seizures in DBA/2 mice"; Naunyn-Schmiedeberg's Arch Pharmacol (2001) 363 :330-336.
European Search Report Jan. 30, 2013.
P. Hewawasam et al.,"The synthesis and structure-activity relationships of 3-amino-4benzylquinolin-2-ones: discovery of novel KCNQ2 channel openers"; Bioorg. Med. Chem. Lett. 14 (2004) 1615-1618.
Dubuisson et al., "The formalin test: a quantitive study of the analgesic effects of morphine, meperidine, and brain stem stimulation in rats and cats"; Pain 1977, 4, 161-174.
Dorange et al. "Recent Progress in the Discovery of Kv7 Modulators", Annual Reports in Medicinal Chemistry, 2011, vol. 46, pp. 53-65.
Brown, D.A., "Some Pharmacological Properties of Neural KCNQ Channels," Neurophysiology 2002, 34 (2-3), 91-94.
Cheung Yiu-Yin, et al. "Discovery of a Series of 2-Phynyl-N-(2-(pyrrolidin-l-yl)phenyl)acetamides as Novel Molecular Switches that Modulate Modes of Kv7.2 . . . " Journal of Medicinal Chemistry, 2012, 55, 6975-6979.
Yu, Haibo, et al.; "Discovery, Synthesis, and Structure-Activity Relationship of a Series of N-Aryl-bicyclo[2.2.1]heptane-2-carboxamides: Characterization of ML213 as a Novel KDNQ2 and KCNQ4 Potassium Channel Opener." ACS Chemical Neuroscience, 2011, 2, 572-577.
Amato, George, et al.; "N-pyridyl and Pyrimidine Benzamides as KCNQ2/Q3 Potassium Channel Openers for the Treatment of Epilepsy."; ACS Medicinal Chemistry Letters, 2011, 2, 481-484.
Fritch, Paul C., et al., "Novel KCNQ2/Q3 Agonists as Potential Therapeutics for Epilepsy and Neuropathic Pain"; Journal of Medicinal Chemistry, 2010, 53, 887-896.
Hu, Hai-ning, et al., "Discovery of a retigabine derivative that inhibits KDNQ2 potassium channels" Acta Pharmacologica Sinica 2013, 34, 1359-1366.
Dorwald, "Side Reactions in Organic Synthesis: A Guide to Successful Synthesis Design" 2005 Wiley-VCH Verlag GmbH & Co. KGaA, Wienheim, Chapter 1, pp. 1-16.
Nielsen et al; "Pharmacological characterisation of acid-induced muscle allodynia in rats"; European Journal of Pharmacology 487 (2004) ppf. 93-103.

* cited by examiner

SPECIFIC CARBOXAMIDES AS KCNQ2/3 MODULATORS

This application claims priority of U.S. Provisional Patent Application No. 61/730,529, filed on Nov. 28, 2012, and European Patent Application No. 12007992.6, filed on Nov. 28, 2012, the entire contents of which patent applications are incorporated herein by reference.

The invention relates to specific carboxamides, to processes for their preparation, to medicaments comprising these compounds and to the use of these compounds in the preparation of medicaments.

The treatment of pain, in particular of neuropathic pain, is of great importance in medicine. There is a worldwide need for effective pain therapies. The urgent need for action for a target-orientated treatment of chronic and non-chronic states of pain appropriate for the patient, by which is to be understood the successful and satisfactory treatment of pain for the patient, is also documented in the large number of scientific works which have recently been published in the field of applied analgesics and of fundamental research into nociception.

A pathophysiological feature of chronic pain is the over-excitability of neurons. Neuronal excitability is influenced decisively by the activity of $K^+$ channels, since these determine decisively the resting membrane potential of the cell and therefore the excitability threshold. Heteromeric $K^+$ channels of the molecular subtype KCNQ2/3 (Kv7.2/7.3) are expressed in neurons of various regions of the central (hippocampus, amygdala) and peripheral (dorsal root ganglia) nervous system and regulate the excitability thereof. Activation of KCNQ2/3 $K^+$ channels leads to a hyperpolarization of the cell membrane and, accompanying this, to a decrease in the electrical excitability of these neurons. KCNQ2/3-expressing neurons of the dorsal root ganglia are involved in the transmission of nociceptive stimuli from the periphery into the spinal marrow (Passmore et al., J. Neurosci. 2003; 23(18): 7227-36).

It has accordingly been possible to detect an analgesic activity in preclinical neuropathy and inflammatory pain models for the KCNQ2/3 agonist retigabine (Blackburn-Munro and Jensen, Eur J. Pharmacol. 2003; 460(2-3); 109-16; post et al., Naunyn Schmiedebergs Arch Pharmacol 2004; 369(4): 382-390).

The KCNQ2/3 $K^+$ channel thus represents a suitable starting point for the treatment of pain; in particular of pain selected from the group consisting of chronic pain, neuropathic pain, inflammatory pain and muscular pain (Nielsen et al., Eur J. Pharmacol. 2004; 487(1-3): 93-103), in particular of neuropathic and inflammatory pain.

Moreover, the KCNQ2/3 $K^+$ channel is a suitable target for therapy of a large number of further diseases, such as, for example, migraine (US2002/0128277), cognitive diseases (Gribkoff, Expert Opin Ther Targets 2003; 7(6): 737-748), anxiety (Korsgaard et al., J Pharmacol Exp Ther. 2005, 14(1): 282-92), epilepsy (Wickenden et al., Expert Opin Ther Pat 2004; 14(4): 457-469; Gribkoff, Expert Opin Ther Targets 2008, 12(5): 565-81; Miceli et al., Curr Opin Pharmacol 2008, 8(1): 65-74), urinary incontinence (Streng et al., J Urol 2004; 172: 2054-2058), dependency (Hansen et al., Eur J Pharmacol 2007, 570(1-3): 77-88), mania/bipolar disorders (Dencker et al., Epilepsy Behav 2008, 12(1): 49-53), dystonia-associated dyskinesias (Richter et al., Br J Pharmacol 2006, 149(6): 747-53).

There is a need for further compounds with comparable or better properties, not only in respect of affinity for KCNQ2/3 as such (potency, efficacy).

For example, it can be advantageous to improve the metabolic stability, the solubility in aqueous media or the permeability of the compounds. These factors can have a positive effect on the oral bioavailability or can change the PK/PD (pharmacokinetic/pharmacodynamic) profile, which can lead, for example, to a more advantageous duration of action.

A weak or non-existent interaction with transporter molecules, which are involved in the uptake and excretion of medicaments, is also to be categorized as an indication of improved bioavailability and low medicament interactions. Further, interactions with the enzymes that are involved in the degradation and excretion of medicaments should also be as low as possible, because such test results likewise indicate that low or no medicament interactions at all are to be expected.

It can also be advantageous for the compounds to exhibit a high selectivity in respect of other receptors of the KCNQ family (specificity), for example in respect of KCNQ1, KCNQ3/5 or KCNQ4. A high selectivity can have a positive effect on the side-effect profile. For example, it is known that compounds which (also) bind to KCNQ1 involve a high risk of cardiac side-effects, for which reason high selectivity in respect of KCNQ1 can be desirable. However, a high selectivity in respect of other receptors can also be advantageous. A low affinity for the hERG ion channel or for the L-type calcium ion channel (phenylalkylamine, benzothiazepine, dihydropyridine binding sites) can be advantageous because those receptors are associated with the occurrence of cardiac side-effects. Overall, an improved selectivity in respect of the binding to other endogenous proteins (i.e. e.g. receptors or enzymes) can lead to an improvement in the side-effect profile and hence to improved tolerability.

An object of the invention was, therefore, to provide novel compounds which have advantages over the compounds of the prior art. The compounds should be suitable in particular as pharmacological active ingredients in medicaments, especially in medicaments for the treatment of disorders or diseases that are mediated at least in part by KCNQ2/3 $K^+$ channels.

That object is achieved by the subject-matter described hereinbelow.

Substituted aryl- or heteroaryl-amides which are suitable as antagonists of the $EP_4$ receptor are known from the prior art (WO 2005/105733). Also known are compounds which are suitable as inhibitors of the DPP-IV enzyme (WO 2007/015767) and of the 11-β-HSD1 enzyme (WO 2008/012532). 2-substituted nicotinamides are known as KCNQ modulators from WO2009/036938 and WO2010/102809.

It has been found, surprisingly, that carboxamides of the general formula (I) below are suitable for the treatment of pain. It has further been found, surprisingly, that carboxamides of the general formula (I) below also have an excellent affinity for the KCNQ2/3 $K^+$ channel and are therefore suitable for the treatment of disorders or diseases that are mediated at least in part by KCNQ2/3 $K^+$ channels. The carboxamides thereby act as modulators, that is to say agonists or antagonists, of the KCNQ2/3 $K^+$ channel.

In a first aspect, the invention provides a compound of the general formula (I)

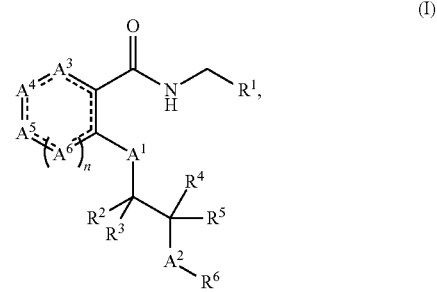

wherein $A^1$ represents $CR^{10}R^{11}$ or S;

$A^2$ represents $CR^{12}R^{13}$, $C(=O)$, O, S, $S(=O)$ or $S(=O)_2$;

$A^3$, $A^4$ and $A^5$ independently of each other represent $CR^7$, N, O, S or $NR^8$, $A^6$ represents $CR^7$ or N, and n denotes 0 or 1, with the proviso, that if n denotes 0, then precisely one of $A^3$, $A^4$ and $A^5$ represents O, S or $NR^8$, or if n denotes 1, then $A^3$, $A^4$ and $A^5$ independently of each other represent $CR^7$ or N;

and with the proviso, that if n denotes 1 and $A^3$, $A^4$ and $A^5$ each represent $CR^7$, then $A^6$ does not represent N;

$R^1$ represents $C_{1-10}$-aliphatic residue, unsubstituted or mono- or polysubstituted;

$C_{3-10}$-cycloaliphatic residue or 3 to 10 membered heterocycloaliphatic residue, in each case unsubstituted or mono- or polysubstituted and in each case optionally linked via a $C_{1-4}$-aliphatic group, which in turn may be unsubstituted or mono- or polysubstituted; aryl or heteroaryl, in each case unsubstituted or mono- or polysubstituted and in each case optionally linked via a $C_{1-8}$-aliphatic group, which in turn may be unsubstituted or mono- or polysubstituted;

$R^2$, $R^3$, $R^4$, $R^5$, $R^{10}$, $R^{11}$, $R^{12}$ and $R^{13}$ each independently of the others represents H; F; Cl; Br; I; $NO_2$; $CF_3$; CN; OH; $OCF_3$; SH; $SCF_3$; $C_{1-10}$-aliphatic residue, $O—C_{1-10}$-aliphatic residue or $S—C_{1-10}$-aliphatic residue, in each case saturated or unsaturated, branched or unbranched, unsubstituted or mono- or poly-substituted;

or $C_{3-10}$-cycloaliphatic residue, saturated or unsaturated, branched or unbranched, unsubstituted or mono- or poly-substituted;

or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{12}$ and $R^{13}$, together with the carbon atom(s) joining them, form a $C_{3-10}$-cycloaliphatic residue or a 3 to 10 membered heterocycloaliphatic residue, in each case saturated or unsaturated, unsubstituted or mono- or poly-substituted; wherein the remaining substituents $R^2$, $R^3$, $R^4$, $R^5$, $R^{10}$, $R^{11}$, $R^{12}$ and $R^{13}$ in each case have the meaning given above;

$R^6$ represents $C_{3-10}$-cycloaliphatic residue or 3 to 10 membered heterocycloaliphatic residue, in each case saturated or unsaturated, unsubstituted or mono- or poly-substituted;

or represents an aryl or a heteroaryl, in each case unsubstituted or mono- or poly-substituted;

each $R^7$ is selected independently from the group consisting of

H; F; Cl; CN; $CF_3$; $CHF_2$; $CH_2F$; $OCF_3$; $OCHF_2$; $OCH_2F$; $SCF_3$; $O—C_{1-4}$-aliphatic residue, $C_{1-4}$-aliphatic residue or $S(=O)_2—C_{1-4}$-aliphatic residue, wherein the $C_{1-4}$-aliphatic residue in each case may be saturated or unsaturated, branched or unbranched, unsubstituted or mono- or poly-substituted;

and $R^8$ represents H or $C_{1-4}$-aliphatic residue, wherein the aliphatic residue may be saturated or unsaturated, branched or unbranched, unsubstituted or mono- or poly-substituted;

in which an "aliphatic group" and "aliphatic residue" may in each case be branched or unbranched, saturated or unsaturated, in which a "cycloaliphatic residue" and a "heterocycloaliphatic residue" may in each case be saturated or unsaturated, in which "mono- or polysubstituted" with respect to an "aliphatic group", an "aliphatic residue", a "cycloaliphatic residue" and a "heterocycloaliphatic residue" relates, with respect to the corresponding residues or groups, to the substitution of one or more hydrogen atoms each independently of one another by at least one substituent selected from the group consisting of F, Cl, Br, I, $NO_2$, $NH_2$, $NH(C_{1-4}$-aliphatic residue), $N(C_{1-4}$-aliphatic residue$)_2$, $NH—C(=O)—C_{1-4}$ aliphatic residue, $N(C_{1-4}$ aliphatic residue$)-C(=O)—C_{1-4}$ aliphatic residue, $NH—S(=O)_2—C_{1-4}$ aliphatic residue, $N(C_{1-4}$ aliphatic residue$)-S(=O)_2—C_{1-4}$ aliphatic residue, $=O$, OH, $OCF_3$, $O—C_{1-4}$-aliphatic residue, $O—C(=O)—C_{1-4}$-aliphatic residue, SH, $SCF_3$, $S—C_{1-4}$-aliphatic residue, $S(=O)_2OH$, $S(=O)_2—C_{1-4}$-aliphatic residue, $S(=O)_2—O—C_{1-4}$-aliphatic residue, $S(=O)_2—NH(C_{1-4}$-aliphatic residue), $S(=O)_2—N(C_{1-4}$-aliphatic residue$)_2$, CN, $CF_3$, CHO, COOH, $C_{1-4}$-aliphatic residue, $C(=O)—C_{1-4}$-aliphatic residue, $C(=O)—O—C_{1-4}$-aliphatic residue, $C_{3-6}$-cycloaliphatic residue, 3 to 7 membered heterocycloaliphatic residue, benzyl, aryl, heteroaryl, $C(=O)NH_2$, a $C(=O)—NH(C_{1-4}$-aliphatic residue) and $C(=O)—N(C_{1-4}$-aliphatic residue$)_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

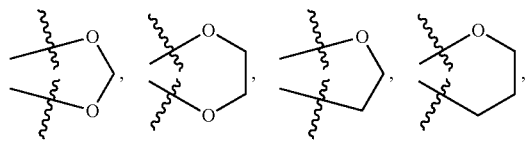 [SMILES: *OCO* ; *OCCO* ; *CCO* ; *CCCO*]

$NH(C_{1-4}$-aliphatic residue), $N(C_{1-4}$-aliphatic residue$)_2$, $NH—C(=O)—C_{1-4}$-aliphatic residue, $N(C_{1-4}$aliphatic residue$)-C(=O)—C_{1-4}$aliphatic residue, $NH—S(=O)_2—C_{1-4}$aliphatic residue, $N(C_{1-4}$aliphatic residue$)-S(=O)_2—C_{1-4}$ aliphatic residue, OH, $OCF_3$, $O—C_{1-4}$-aliphatic residue, $O—C(=O)—C_{1-4}$-aliphatic residue, SH, $SCF_3$, $S—C_{1-4}$-aliphatic residue, $S(=O)_2OH$, $S(=O)_2—C_{1-4}$-aliphatic residue, $S(=O)_2—O—C_{1-4}$-aliphatic residue, $S(=O)_2—NH(C_{1-4}$-aliphatic residue), $S(=O)_2—N(C_{1-4}$-aliphatic residue$)_2$, CN, $CF_3$, $C(=O)H$, $C(=O)OH$, $C_{1-4}$-aliphatic residue, $C(=O)—C_{1-4}$-aliphatic residue, $C(=O)—O—C_{1-4}$-aliphatic residue, $C_{3-6}$-cycloaliphatic residue, 3 to 7 membered heterocycloaliphatic residue, benzyl, aryl, heteroaryl, $C(=O)NH_2$, $C(=O)—NH(C_{1-4}$-aliphatic residue) and $C(=O)—N(C_{1-4}$-aliphatic residue$)_2$;

in the form of an individual single stereoisomer or a mixture of the stereoisomers in any mixing ratio, and/or in the form of a free compound, a solvate and/or a physiologically acceptable salt.

Within the scope of this invention, the terms "aliphatic residue" or "aliphatic group" include acyclic saturated or unsaturated aliphatic hydrocarbon radicals, which can be branched or unbranched as well as unsubstituted or mono- or poly-substituted, having from 1 to 10 or from 1 to 8 or from 1 to 6 or from 1 to 4 or from 1 to 2 or from 2 to 6 carbon atoms, that is to say $C_{1-10}$-alkanyls, $C_{2-10}$-alkenyls and $C_{2-10}$-alkynyls or $C_{1-8}$-alkanyls, $C_{2-8}$-alkenyls and $C_{2-8}$-alkynyls or $C_{1-6}$-alkanyls, $C_{2-6}$-alkenyls and $C_{2-6}$-alkynyls or $C_{1-4}$-alkanyls, $C_{2-4}$-alkenyls and $C_{2-4}$-alkynyls or $C_{1-2}$-alkanyls, $C_2$-alkenyls and $C_2$-alkynyls or $C_{2-6}$-alkanyls, $C_{2-6}$-alkenyls and $C_{2-6}$-alkynyls. Alkenyls contain at least one C—C double bond and alkynyls contain at least one C—C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl (vinyl), ethynyl, propenyl (—CH$_2$CH═CH$_2$, —CH═CHCH$_3$, —C(═CH$_2$)CH$_3$), propynyl (—CH$_2$C≡CH, —C≡CCH$_3$), butenyl, butynyl, pentenyl, pentynyl, hexenyl and hexynyl, heptenyl, heptynyl, octenyl, octynyl, nonenyl, nonynyl, decenyl and decynyl.

For the purposes of this invention, the terms "cycloaliphatic residue" or "$C_{3-10}$-cycloaliphatic residue", "$C_{3-8}$-cycloaliphatic residue" and "$C_{3-6}$-cycloaliphatic residue" denote cyclic aliphatic hydrocarbons having 3, 4, 5, 6, 7, 8, 9 or 10 carbon atoms or having 3, 4, 5, 6, 7 or 8 carbon atoms or having 3, 4, 5 or 6 carbon atoms, wherein the hydrocarbons can be saturated or unsaturated (but not aromatic), unsubstituted or mono- or poly-substituted. The bonding of the cycloaliphatic residue to the general structure of higher order can take place via any desired and possible ring member of the cycloalkyl radical. The cycloaliphatic residue can also be fused with further saturated, (partially) unsaturated, (hetero) cycloaliphatic, aromatic or heteroaromatic ring systems, that is to say with cycloaliphatic residue, heterocycloaliphatic residue, aryl or heteroaryl, which can themselves be unsubstituted or mono- or poly-substituted. The cycloaliphatic residue radicals can further be bridged one or more times, as, for example, in the case of adamantyl, bicyclo[2.2.1]heptyl or bicyclo[2.2.2]octyl. Cycloalkyl is preferably selected from the group comprising cyclopropyl, cyclobutyl, cyclopentyl, cyclopentenyl, cyclohexyl, cyclohexenyl, cycloheptyl, cycloheptenyl, cyclooctyl, cyclooctenyl cyclononyl, cyclodecyl, adamantyl as well as

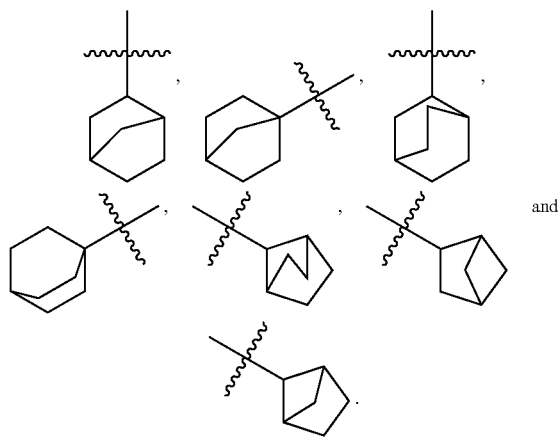

The term "3 to 10 membered heterocycloaliphatic residue" or "3 to 7 membered heterocycloaliphatic residue" or "heterocycloaliphatic residue" includes aliphatic saturated or unsaturated (but not aromatic) heterocycloaliphatic residues having preferentially from three to ten, that is to say 3, 4, 5, 6, 7, 8, 9 or 10, ring members or from three to seven, that is to say 3, 4, 5, 6 or 7, ring members in which at least one carbon atom, optionally also two or three carbon atoms, has been replaced by a heteroatom or heteroatom group in each case selected independently of one another from the group consisting of O, S, S(═O), S(═O)$_2$, N, NH and N($C_{1-8}$alkyl), preferably N(CH$_3$), wherein the ring members can be unsubstituted or mono- or poly-substituted. The bonding of the heterocycloaliphatic residue to the general structure of higher order can take place via any desired and possible ring member of the heterocycloaliphatic residue. The heterocycloaliphatic residues can also be fused with further saturated, (partially) unsaturated (hetero)cycloaliphatic or aromatic or heteroaromatic ring systems, that is to say with cycloaliphatic residue, heterocycloaliphatic residue, aryl or heteroaryl, which can themselves be unsubstituted or mono- or poly-substituted. Heterocycloaliphatic residues are preferably selected from the group comprising azetidinyl, aziridinyl, azepanyl, azocanyl, diazepanyl, dithiolanyl, dihydroquinolinyl, dihydropyrrolyl, dioxanyl, dioxolanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl.

Within the scope of this invention, the term "aryl" denotes aromatic hydrocarbons having up to 14 ring members, inter alia phenyls and naphthyls. Each aryl radical can be unsubstituted or mono- or poly-substituted, it being possible for the aryl substituents to be identical or different and to be in any desired and possible position of the aryl. The aryl can be bonded to the general structure of higher order via any desired and possible ring member of the aryl radical. The aryl radicals can also be fused with further saturated, (partially) unsaturated, (hetero)cycloaliphatic, aromatic or heteroaromatic ring systems, that is to say with cycloaliphatic residue, heterocycloaliphatic residue, aryl or heteroaryl, which can themselves be unsubstituted or mono- or poly-substituted. Examples of fused aryl radicals are benzodioxolanyl and benzodioxanyl. Aryl is preferably selected from the group containing phenyl, 1-naphthyl and 2-naphthyl, each of which can be unsubstituted or mono- or poly-substituted. A particularly preferred aryl is phenyl, unsubstituted or mono- or poly-substituted.

The term "heteroaryl" denotes a 5- or 6-membered cyclic aromatic radical which contains at least 1 heteroatom, optionally also 2, 3, 4 or 5 heteroatoms, wherein the heteroatoms are in each case selected independently of one another from the group S, N and O and the heteroaryl radical can be unsubstituted or mono- or poly-substituted; in the case of substitution on the heteroaryl, the substituents can be identical or different and can be in any desired and possible position of the heteroaryl. Bonding to the general structure of higher order can take place via any desired and possible ring member of the heteroaryl radical. The heteroaryl can also be part of a bi- or poly-cyclic system having up to 14 ring members, wherein the ring system can be formed with further saturated, (partially) unsaturated, (hetero)-cycloaliphatic residue or aromatic or heteroaromatic rings, that is to say with cycloaliphatic residue, heterocycloaliphatic residue, aryl or heteroaryl, which can themselves be unsubstituted or mono- or poly-substituted. It is preferred for the heteroaryl radical to be selected from the group comprising benzo-furanyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl and thienyl are particularly preferred.

Within the scope of the invention, the expressions "linked via $C_{1-4}$-aliphatic group" in relation to aryl, heteroaryl, heterocycloaliphatic residue or cycloaliphatic residue is understood that $C_{1-4}$-aliphatic group and aryl or heteroaryl or heterocycloaliphatic residue or cycloaliphatic residue have the meanings defined above and the aryl or heteroaryl or heterocycloaliphatic residue or cycloaliphatic residue is bonded to the general structure of higher order via a $C_{1-4}$-aliphatic group. The aliphatic group can in all cases be saturated or unsaturated, branched or unbranched, unsubstituted or mono- or poly-substituted. The $C_{1-4}$-aliphatic group is preferably selected from $C_{1-4}$-alkyl groups, preferably from the group comprising of —$CH_2$—, —$CH_2CH_2$—, —$CH(CH_3)$—, —$CH_2CH_2CH_2$—, —$CH(CH_3)CH_2$—, —$CH(CH_2CH_3)$—, —$CH_2(CH_2)_2CH_2$—, —$CH(CH_3)CH_2CH_2$—, —$CH_2CH(CH_3)CH_2$—, —$CH(CH_3)CH(CH_3)$—, —$CH(CH_2CH_3)CH_2$—, —$C(CH_3)_2CH_2$—, —$CH(CH_2CH_2CH_3)$—, —$C(CH_3)(CH_2CH_3)$—, —CH=CH—, —CH=CHCH_2—, —$C(CH_3)$=$CH_2$—, —CH=CHCH_2CH_2—, —$CH_2CH$=$CHCH_2$—, —CH=CHCH=CH—, —$C(CH_3)$=$CHCH_2$—, —$CHCH_2$—, —CH=$C(CH_3)CH_2$—, —$C(CH_3)$=$C$ ($CH_3$)—, —$C(CH_2CH_3)$=CH—, —C≡C—, —C≡$CCH_2$—, —C≡$CCH_2CH_2$—, —C≡$CCH(CH_3)$—, —$CH_2C$≡$CCH_2$— and —C≡$CC(CH_3)_2$—.

In relation with "aliphatic residue", "aliphatic group", "heterocycloaliphatic residue" and "cycloaliphatic residue", the expression "mono- or poly-substituted" is understood as meaning within the scope of this invention the substitution of one or more hydrogen atoms one or more times, for example two, three or four times, in each case independently of one another, by substituents selected from the group comprising F, Cl, Br, I, NO_2, NH_2, NH($C_{1-4}$-aliphatic residue), N($C_{1-4}$-aliphatic residue)_2, NH—C(=O)—$C_{1-4}$ aliphatic residue, N($C_{1-4}$-aliphatic residue)-C(=O)—$C_{1-4}$ aliphatic residue, NH—S(=O)_2—$C_{1-4}$-aliphatic residue, N($C_{1-4}$-aliphatic residue)-S(=O)_2—$C_{1-4}$-aliphatic residue, =O, OH, OCF_3, O—$C_{1-4}$-aliphatic residue, O—C(=O)—$C_{1-4}$-aliphatic residue, SH, SCF_3, S—$C_{1-4}$-aliphatic residue, S(=O)_2OH, S(=O)_2—$C_{1-4}$-aliphatic residue, S(=O)_2—O—$C_{1-4}$-aliphatic residue, S(=O)_2—NH($C_{1-4}$-aliphatic residue), S(=O)_2—N($C_{1-4}$-aliphatic residue)_2, CN, CF_3, CHO, COOH, $C_{1-4}$-aliphatic residue, C(=O)—$C_{1-4}$-aliphatic residue, C(=O)—O—$C_{1-4}$-aliphatic residue, $C_{3-6}$-cycloaliphatic residue, 3 to 7 membered heterocycloaliphatic residue, benzyl, aryl, heteroaryl, C(=O)NH_2, a C(=O)—NH($C_{1-4}$-aliphatic residue) and C(=O)—N($C_{1-4}$-aliphatic residue)_2; wherein polysubstituted radicals are to be understood as being radicals that are substituted several times, for example two, three or four times, either on different atoms or on the same atom, for example three times on the same carbon atom, as in the case of CF_3 or CH_2CF_3, or at different places, as in the case of CH(OH)—CH=CH—CHCl_2. A substituent can itself optionally be mono- or poly-substituted. Polysubstitution can take place with the same or with different substituents.

Preferred substituents of "aliphatic residue", "aliphatic group", "heterocycloaliphatic residue" or "cycloaliphatic residue" are selected from the group comprising F, Cl, Br, NH_2, NH($C_{1-4}$-aliphatic residue), N($C_{1-4}$-aliphatic residue)_2, NH—C(=O)—$C_{1-4}$-aliphatic residue, NH—S(=O)_2—$C_{1-4}$-aliphatic residue, =O, OH, OCF_3, O—$C_{1-4}$-aliphatic residue, O—C(=O)—$C_{1-4}$-aliphatic residue, S(=O)_2—$C_{1-4}$-aliphatic residue, S(=O)_2—NH($C_{1-4}$-aliphatic residue), S(=O)_2—N($C_{1-4}$-aliphatic residue)_2, CN, CF_3, COOH, $C_{1-4}$-aliphatic residue, C(=O)—$C_{1-4}$-aliphatic residue, $C_{3-6}$-cycloaliphatic residue, 3 to 7 membered heterocycloaliphatic residue, C(=O)NH_2, C(=O)—NH($C_{1-4}$-aliphatic residue) and C(=O)—N($C_{1-4}$-aliphatic residue)_2.

In relation with "aryl" and "heteroaryl", the term "mono- or poly-substituted" is understood within the scope of this invention as meaning the substitution of one or more hydrogen atoms of the ring system one or more times, for example two, three or four times, in each case independently of one another, by substituents selected from the group comprising F, Cl, Br, I, NO_2, NH_2,

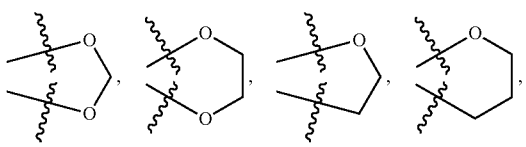 [SMILES: *OCO* ; *OCCO* ; *CCO* ; *CCCO*]

NH($C_{1-4}$-aliphatic residue), N($C_{1-4}$-aliphatic residue)_2, NH—C(=O)—$C_{1-4}$-aliphatic residue, N($C_{1-4}$-aliphatic residue)-C(=O)—$C_{1-4}$-aliphatic residue, NH—S(=O)_2—$C_{1-4}$-aliphatic residue, N($C_{1-4}$aliphatic residue)-S(=O)_2—$C_{1-4}$-aliphatic residue, OH, OCF_3, O—$C_{1-4}$-aliphatic residue, O—C(=O)—$C_{1-4}$-aliphatic residue, SH, SCF_3, S—$C_{1-4}$-aliphatic residue, S(=O)_2OH, S(=O)_2—$C_{1-4}$-aliphatic residue, S(=O)_2—O—$C_{1-4}$-aliphatic residue, S(=O)_2—NH($C_{1-4}$-aliphatic residue), S(=O)_2—N($C_{1-4}$-aliphatic residue)_2, CN, CF_3, C(=O)H, C(=O)OH, $C_{1-4}$-aliphatic residue, C(=O)—$C_{1-4}$-aliphatic residue, C(=O)—O—$C_{1-4}$-aliphatic residue, $C_{3-6}$-cycloaliphatic residue, 3 to 7 membered heterocycloaliphatic residue, benzyl, aryl, heteroaryl, C(=O)NH_2, C(=O)—NH($C_{1-4}$-aliphatic residue) and C(=O)—N($C_{1-4}$-aliphatic residue)_2; on one atom or optionally on different atoms, wherein a substituent can itself optionally be mono- or poly-substituted. Polysubstitution is carried out with the same or with different substituents.

Preferred "aryl" and "heteroaryl" substituents are F; Cl; Br; CF_3; CN; $C_{1-4}$-aliphatic residue; phenyl; naphthyl; pyridyl; thienyl; furyl; $C_{3-6}$-cycloaliphatic residue; 3 to 7 membered heterocycloaliphatic residue; C(=O)—$C_{1-4}$-aliphatic residue; CO_2H; C(=O)—O—$C_{1-4}$-aliphatic residue; CONH_2; C(=O)—NH($C_{1-4}$-aliphatic residue); C(=O)—N ($C_{1-4}$-aliphatic residue)_2; OH; O—$C_{1-4}$-aliphatic residue; OCF_3; O—C(=O)—$C_{1-4}$-aliphatic residue; NH_2; NH($C_{1-4}$-aliphatic residue); N($C_{1-4}$-aliphatic residue)_2; N(H)C (=O)—$C_{1-4}$-aliphatic residue; S—$C_{1-8}$-alkyl; SCF_3; S(=O)_2$C_{1-4}$-aliphatic residue; S(=O)_2—N(H)$C_{1-4}$-aliphatic residue.

The compounds according to the invention are defined by substituents, for example by $R^A$, $R^B$ and $R^C$ (1st generation substituents), which are themselves optionally substituted (2nd generation substituents). Depending on the definition, these substituents of the substituents can in turn themselves be substituted (3rd generation substituents). If, for example, $R^A$=aryl (1st generation substituent), aryl can itself be substituted, for example by $C_{1-4}$-aliphatic residue (2nd generation substituent). This yields the functional group aryl-$C_{1-4}$-aliphatic residue. $C_{1-4}$-aliphatic residue can then in turn itself be substituted, for example by Cl (3rd generation substituent). Overall, this then yields the functional group aryl-$C_{1-4}$-aliphatic residue-Cl.

In a preferred embodiment, however, the 3rd generation substituents cannot themselves be substituted, that is to say there are no 4th generation substituents.

In another preferred embodiment, the 2nd generation substituents cannot themselves be substituted, that is to say there are not even any 3rd generation substituents. In other words, in this embodiment, for example in the case of the general formula (I), the functional groups for $R^1$ to $R^{14}$ can in each case optionally be substituted, but the substituents in each case cannot themselves be substituted.

In some cases, the compounds according to the invention are defined by substituents which are or carry an aryl or heteroaryl radical, in each case unsubstituted or mono- or poly-substituted, or which, together with the carbon atom(s) or heteroatom(s) joining them as ring member(s), form a ring, for example an aryl or heteroaryl, in each case unsubstituted or mono- or poly-substituted. Both these aryl or heteroaryl radicals and the aromatic ring systems so formed can optionally be fused with $C_{3-10}$-cycloaliphatic residue or heterocycloaliphatic residue, in each case saturated or unsaturated, that is to say with a $C_{3-10}$-cycloaliphatic residue such as cyclopentyl or with a heterocycloaliphatic residue such as morpholinyl, it being possible for the $C_{3-10}$-cycloaliphatic residue or heterocycloaliphatic residue radicals so fused to be unsubstituted or mono- or poly-substituted.

In some cases, the compounds according to the invention are defined by substituents which are or carry a $C_{3-10}$-heterocycloaliphatic residue or heterocycloaliphatic residue, in each case unsubstituted or mono- or poly-substituted, or which, together with the carbon atom(s) or heteroatom(s) joining them as ring member(s), form a ring, for example a $C_{3-10}$-cycloaliphatic residue or heterocycloaliphatic residue, in each case unsubstituted or mono- or poly-substituted. Both these $C_{3-10}$-cycloaliphatic or heterocycloaliphatic residue and the aliphatic ring systems formed can optionally be fused with aryl or heteroaryl, that is to say with an aryl such as phenyl or with a heteroaryl such as pyridyl, it being possible for the aryl or heteroaryl radicals so fused to be unsubstituted or mono- or poly-substituted.

Within the scope of the present invention, the symbol

used in formulae denotes a linking of a corresponding radical to the general structure of higher order.

The expression "salt formed with a physiologically acceptable acid" is understood within the scope of this invention as meaning salts of the active ingredient in question with inorganic or organic acids that are physiologically acceptable—in particular when used in humans and/or mammals. The hydrochloride is particularly preferred.

Physiologically acceptable salts with cations or bases are salts of the compound in question—in the form of the anion with at least one, preferably inorganic cation—that are physiologically acceptable—in particular when used in humans and/or mammals.

One embodiment of the first aspect of the invention is a compound of the general formula (I), characterized in that
$A^1$ represents $CR^{10}R^{11}$ or S;
$A^2$ represents $CR^{12}R^{13}$, $C(=O)$, O, S, $S(=O)$ or $S(=O)_2$;
$A^3$, $A^4$ and $A^5$ independently of each other represent $CR^7$, N, O, S or $NR^8$,
$A^6$ represents $CR^7$ or N, and
n denotes 0 or 1,
with the proviso, that
if n denotes 0, then precisely one of $A^3$, $A^4$ and $A^5$ represents O, S or $NR^8$, or
if n denotes 1, then $A^3$, $A^4$ and $A^5$ independently of each other represent $CR^7$ or N;

and with the proviso, that if n denotes 1 and $A^3$, $A^4$ and $A^5$ each represent $CR^7$, then $A^6$ does not represent N;
$R^1$ denotes a $C_{1-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and $C(=O)OH$,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, $C(=O)OH$, $C_{3-6}$-cycloaliphatic residue and a 3 to 7 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and $C(=O)OH$,
and wherein the $C_{3-10}$-cycloaliphatic residue or the 3 to 10 membered heterocycloaliphatic residue may in each case optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and $C(=O)OH$,
or denotes aryl or heteroaryl, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, $C(=O)OH$, $C(=O)CH_3$, $C(=O)C_2H_5$, $C(=O)OCH_3$, $C(=O)OC_2H_5$, $C_{3-6}$ cycloaliphatic residue, 3 to 6 membered heterocycloaliphatic residue,

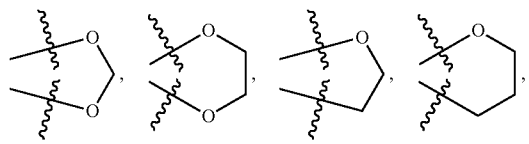 [SMILES: *OCO* ; *OCCO* ; *CCO* ; *CCCO*]

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, $OCH_2CH_2OH$, $OCH_2OCH_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$, C(=O)$OC_2H_5$, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the aryl or the heteroaryl residue may in each case be optionally linked via a $C_{1-4}$-aliphatic group, which in turn may be unsubstituted or mono- or polysubstituted with at least one substituent selected from the group consisting of F, Cl, Br, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN and C(=O)OH, $R^2$, $R^3$, $R^4$, $R^5$, $R^{10}$, $R^{11}$, $R^{12}$ and $R^{13}$ each independently of the others represents H; F; Cl; Br; I; $NO_2$; $CF_3$; CN; OH; $OCF_3$; SH; $SCF_3$; $C_{1-4}$-aliphatic residue, O—$C_{1-4}$-aliphatic residue or S—$C_{1-4}$-aliphatic residue, in each case saturated or unsaturated, branched or unbranched, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, or a $C_{3-10}$-cycloaliphatic residue, saturated or unsaturated, branched or unbranched, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-10}$-cycloaliphatic residue may in each case optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{12}$ and $R^{13}$, together with the carbon atom(s) joining them, form a $C_{3-10}$-cycloaliphatic residue or a 3 to 10 membered heterocycloaliphatic residue, in each case saturated or unsaturated and in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-10}$-cycloaliphatic residue or the 3 to 10 membered heterocycloaliphatic residue may in each case optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the remaining substituents $R^2$, $R^3$, $R^4$, $R^5$, $R^{10}$, $R^{11}$, $R^{12}$ and $R^{13}$ in each case have the meaning given above;

$R^6$ represents a $C_{3-10}$-cycloaliphatic residue or a 3 to 10 membered heterocycloaliphatic residue, in each case saturated or unsaturated and in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, $C_{3-6}$-cycloaliphatic residue and 3 to 7 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the $C_{3-10}$-cycloaliphatic residue or the 3 to 10 membered heterocycloaliphatic residue may in each case optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, or represents aryl or heteroaryl, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$, C(=O)$OC_2H_5$, $C_{3-6}$-cycloaliphatic residue, 3 to 7 membered heterocycloaliphatic residue,

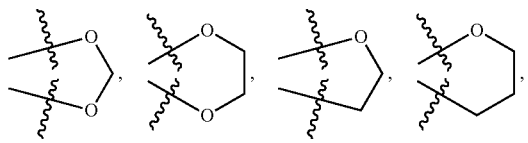 [SMILES: *OCO* ; *OCCO* ; *CCO* ; *CCCO*]

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, $OCH_2CH_2OH$, $OCH_2OCH_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$ and C(=O)$OC_2H_5$, and wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the aryl or the heteroaryl residue may in each case be optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, =O, O—$C_{1-4}$-aliphatic residue, $OCF_3$, SH, $SCF_3$, S—$C_{1-4}$-aliphatic residue, $CF_3$, CN and C(=O)OH, each $R^7$ independently of each other represents H, F; Cl; CN; $CF_3$; $CHF_2$; $CH_2F$; $OCF_3$; $OCHF_2$; $OCH_2F$; $SCF_3$; a O—$C_{1-4}$-aliphatic residue, a $C_{1-4}$-aliphatic residue or a S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and $R^8$ represents H or $C_{1-4}$-aliphatic residue, wherein the $C_{1-4}$-aliphatic residue may be unsubstituted or mono- or polysubstituted with at least one substituent selected from the group consisting of F, Cl, Br, I, OH, $OCF_3$, $CF_3$ and O—$C_{1-4}$-aliphatic residue.

In one embodiment of the invention, the compound of the general formula (I) is characterized in that
$A^1$ represents S and
$A^2$ represents $CR^{12}R^{13}$, S or S(=O)$_2$.

In a preferred embodiment of the invention, the compound of the general formula (I) is characterized in that
$A^1$ represents S and
$A^2$ represents S(=O)$_2$.

In another preferred embodiment of the invention, the compound of the general formula (I) is characterized in that
$A^1$ represents S and
$A^2$ represents $CR^{12}R^{13}$.

In another preferred embodiment of the invention, the compound of the general formula (I) is characterized in that
$A^1$ represents S and
$A^2$ represents $CR^{12}R^{13}$, wherein $R^{12}$ and $R^{13}$ both represent H or both represent F.

In a further preferred embodiment of the invention, the compound of the general formula (I) according to the invention has the general formula (Ia), (Ib), (Ic), (Id), (Ie) or (If):

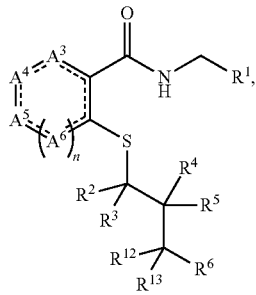

(Ia)

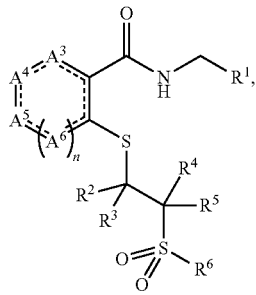

(Ib)

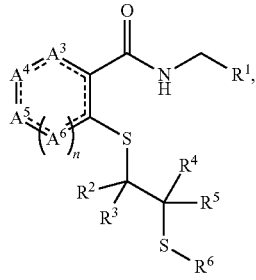

(Ic)

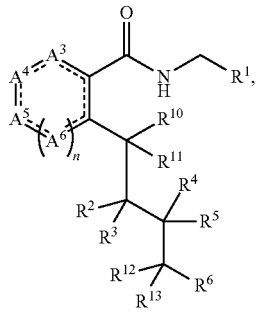

(Id)

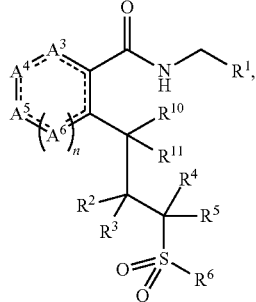

(Ie)

-continued

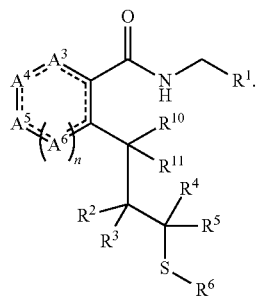

(If)

Compounds of the general formulae (Ia), (Ib) and (Ic) are particularly preferred.

Compounds of the general formula (Ia) are especially preferred.

Particularly, compounds of the general formula (Ia) are preferred, wherein $R^{12}$ and $R^{13}$ both represent H.

Particularly, compounds of the general formula (Ia) are preferred, wherein $R^{12}$ and $R^{13}$ both represent F.

Within the scope of the present invention, the central structural element of general formula (I),

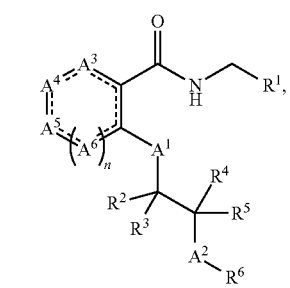

(I)

represents a 5-membered (for n=0) or a 6-membered aryl or heteroaryl residue (for n=1). The residue is aromatic as depicted by the dashed bond presentation.

If n represents 1, then central structural element in general formula (I) represents a 6-membered heteroaryl residue (I-1):

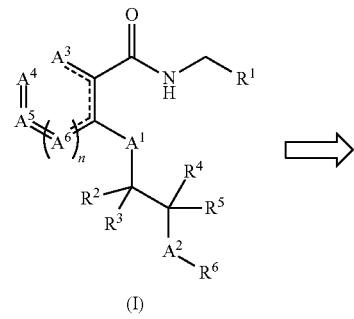

(I-1)

If n represents 0, then the partial structure in general formula (I) represents a 5-membered heteroaryl residue (I-2) or (I-3) or (I-4):

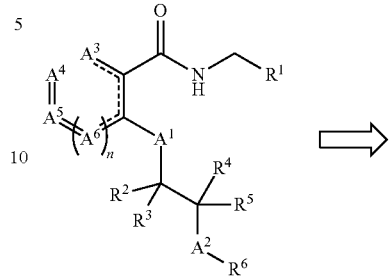

(I)

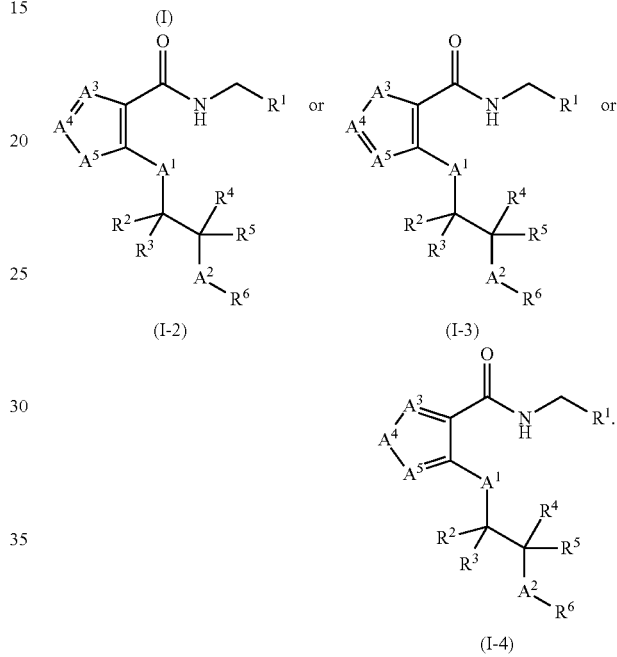

(I-2)    (I-3)

(I-4)

To retain aromaticity of the 5-membered heterocycle, it is understood within the scope of the invention, that, if n denotes 0 and $A^3$ represents O or S or $NR^8$, the compound according to general formula (I) is represented by formula (I-2), that, if n denotes 0 and $A^5$ represents O or S or $NR^8$, the compound according to general formula (I) is represented by formula (I-3), and that, if n denotes 0 and $A^4$ represents O or S or $NR^8$, the compound according to general formula (I) is represented by formula (I-4).

In another embodiment of the invention, the compound according to general formula (I) is characterized in that n denotes 1 and $A^3$ represents $CR^7$, $A^4$ represents $CR^7$, $A^5$ represents $CR^7$ and $A^6$ represents $CR^7$ (formula (I-1a)),

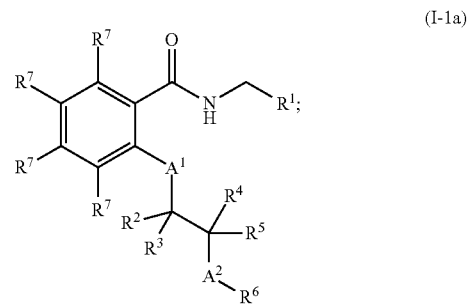

(I-1a)

or n denotes 1 and $A^3$ represents N, $A^4$ represents $CR^7$, $A^5$ represents $CR^7$ and $A^6$ represents $CR^7$ (formula (I-1b)),

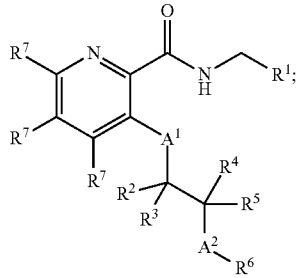
(I-1b)

or n denotes 1 and $A^3$ represents $CR^7$, $A^4$ represents N, $A^5$ represents $CR^7$ and $A^6$ represents $CR^7$ (formula (I-1c)),

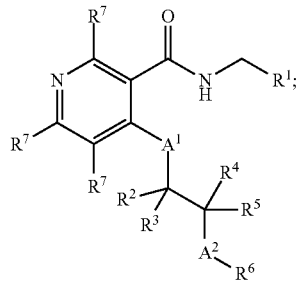
(I-1c)

or n denotes 1 and $A^3$ represents $CR^7$, $A^4$ represents $CR^7$, $A^5$ represents N and $A^6$ represents $CR^7$ (formula (I-1d)),

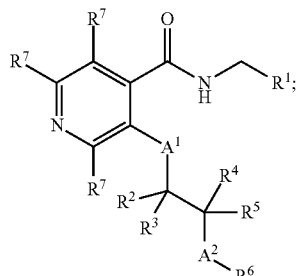
(I-1d)

or n denotes 1 and $A^3$ represents N, $A^4$ represents N, $A^5$ represents $CR^7$ and $A^6$ represents $CR^7$ (formula (I-1e)),

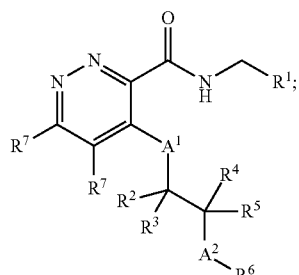
(I-1e)

or n denotes 1 and $A^3$ represents N, $A^4$ represents $CR^7$, $A^5$ represents N and $A^6$ represents $CR^7$ (formula (I-1f)),

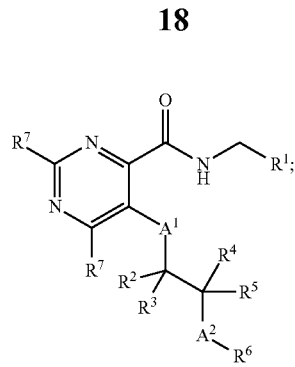
(I-1f)

or n denotes 1 and $A^3$ represents N, $A^4$ represents $CR^7$, $A^5$ represents $CR^7$ and $A^6$ represents N (formula (I-1g)),

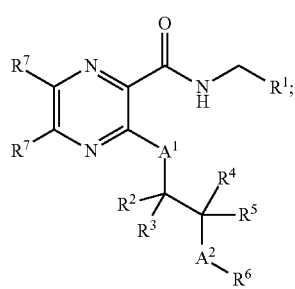
(I-1g)

or n denotes 1 and $A^3$ represents $CR^7$, $A^4$ represents N, $A^5$ represents $CR^7$ and $A^6$ represents N (formula (I-1h)),

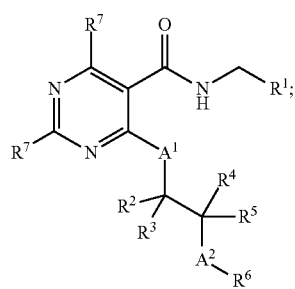
(I-1h)

or n denotes 1 and $A^3$ represents $CR^7$, $A^4$ represents N, $A^5$ represents N and $A^6$ represents $CR^7$ (formula (I-1i)),

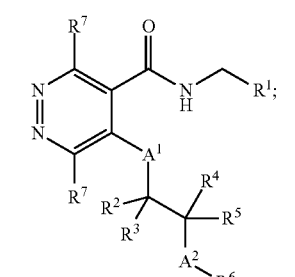
(I-1i)

or n denotes 1 and $A^3$ represents $CR^7$, $A^4$ represents $CR^7$, $A^5$ represents N and $A^6$ represents N (formula (I-1j)), (I-1j)

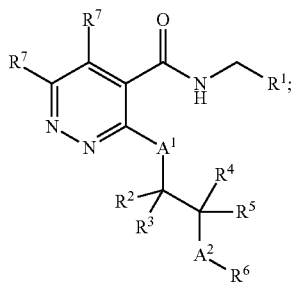

or
n denotes 0 and A³ represents S, A⁴ represents CR⁷ and A⁵ represents CR⁷ (formula (I-3a)), (I-3a)

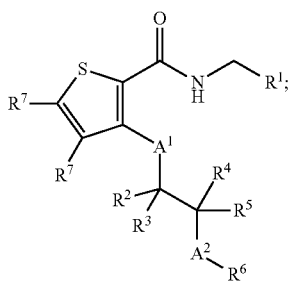

or
n denotes 0 and A³ represents S, A⁴ represents CR⁷ and A⁵ represents N (formula (I-3b)), (I-3b)

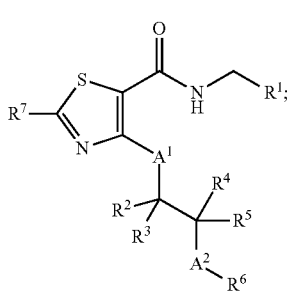

or
n denotes 0 and A³ represents O, A⁴ represents CR⁷ and A⁵ represents CR⁷ (formula (I-3c)), (I-3c)

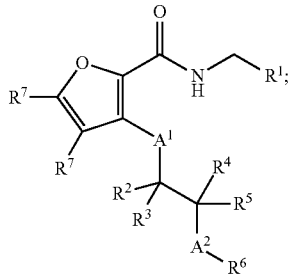

or
n denotes 0 and A³ represents O, A⁴ represents CR⁷ and A⁵ represents N (formula (I-3d)), (I-3d)

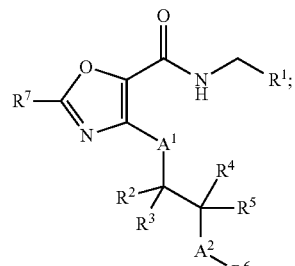

or
n denotes 0 and A³ represents CR⁷, A⁴ represents CR⁷ and A⁵ represents S (formula (I-2a)), (I-2a)

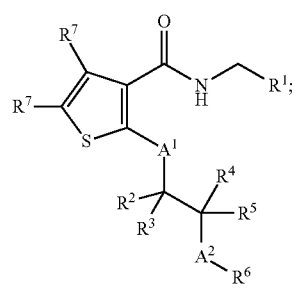

or
n denotes 0 and A³ represents N, A⁴ represents CR⁷ and A⁵ represents S (formula (I-2b)), (I-2b)

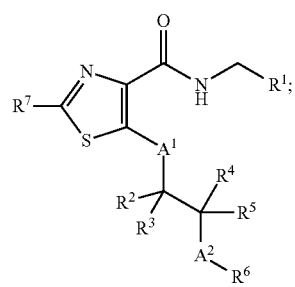

or
n denotes 0 and A³ represents CR⁷, A⁴ represents CR⁷ and A⁵ represents O (formula (I-2c)), (I-2c)

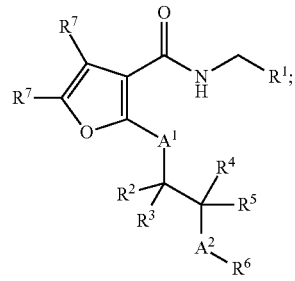

or
n denotes 0 and A³ represents N, A⁴ represents CR⁷ and A⁵ represents O (formula (I-2d)), (I-2d)

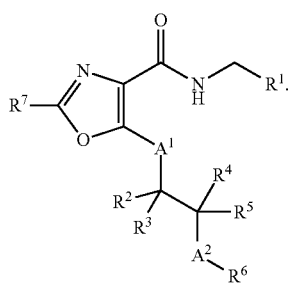

In preferred embodiment of the invention, the compound according to general formula (I) is characterized in that
n denotes 1 and $A^3$ represents $CR^7$, $A^4$ represents $CR^7$, $A^5$ represents $CR^7$ and $A^6$ represents $CR^7$ (formula (I-1a)); or
n denotes 1 and $A^3$ represents N, $A^4$ represents $CR^7$, $A^5$ represents $CR^7$ and $A^6$ represents $CR^7$ (formula (I-1b)); or
n denotes 1 and $A^3$ represents $CR^7$, $A^4$ represents N, $A^5$ represents $CR^7$ and $A^6$ represents $CR^7$ (formula (I-1c)); or
n denotes 1 and $A^3$ represents $CR^7$, $A^4$ represents $CR^7$, $A^5$ represents N and $A^6$ represents $CR^7$(formula (I-1d)); or
n denotes 1 and $A^3$ represents N, $A^4$ represents $CR^7$, $A^5$ represents $CR^7$ and $A^6$ represents N (formula (I-1g)); or
n denotes 1 and $A^3$ represents $CR^7$, $A^4$ represents N, $A^5$ represents $CR^7$ and $A^6$ represents N (formula (I-1h)); or
n denotes 1 and $A^3$ represents $CR^7$, $A^4$ represents $CR^7$, $A^5$ represents N and $A^6$ represents N (formula (I-1j)); or
n denotes 0 and $A^3$ represents S, $A^4$ represents $CR^7$ and $A^5$ represents N (formula (I-3b)).

In a further preferred embodiment, the radical $R^1$ represents
$C_{1-10}$-aliphatic residue, saturated or unsaturated, branched or unbranched, unsubstituted or mono- or poly-substituted by one or more substituents each selected independently of one another from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue,
$C_{3-10}$-cycloaliphatic residue or 3 to 10 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, $C_{3-6}$-cycloaliphatic residue and a 3 to 7 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the $C_{3-10}$-cycloaliphatic residue or the 3 to 10 membered heterocycloaliphatic residue may in each case optionally linked via a $C_{1-4}$-aliphatic group, which in turn may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, or aryl or heteroaryl, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)$CH_3$, C(=O) $C_2H_5$, C(=O)$OCH_3$, C(=O)$OC_2H_5$, $C_{3-6}$ cycloaliphatic residue, 3 to 6 membered heterocycloaliphatic residue,

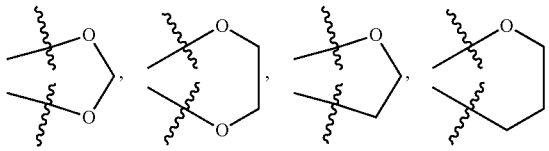

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and O—$C_{1-4}$-aliphatic residue, and
wherein benzyl, phenyl, thienyl, pyridyl, furyl, thiazolyl and oxazolyl may in each case may be unsubstituted or mono- or polysubstituted with at least one substituent selected from the group consisting of F, Cl, Br, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, $OCH_2CH_2OH$, $OCH_2OCH_3$, SH, $SCF_3$, S—$C_{1-4}$-aliphatic residue, $CF_3$, CN, $C_{1-4}$-aliphatic residue, C(=O) OH, C(=O)$CH_3$, C(=O)$C_2H_5$, C(=O)$OCH_3$, C(=O) $OC_2H_5$, and
wherein the $C_{3-6}$-cycloaliphatic residue and the 3 to 7 membered heterocycloaliphatic residue may in each case may be unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH,
and wherein the aryl or the heteroaryl residue may in each case be optionally linked via a $C_{1-4}$-aliphatic group, which in turn may be unsubstituted or mono- or polysubstituted with at least one substituent selected from the group consisting of F, Cl, Br, $NO_2$, $NH_2$, $NH(C_{1-4}$-aliphatic residue), $N(C_{1-4}$-aliphatic residue$)_2$, OH, =O, O—$C_{1-4}$-aliphatic residue, $OCF_3$, SH, $SCF_3$, S—$C_{1-4}$-aliphatic residue, $CF_3$, CN and C(=O)OH.

In a further preferred embodiment, the substituent $R^1$ represents the partial structure (T1)

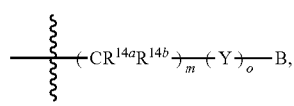
(T1)

wherein
$R^{14a}$ and $R^{14b}$ each independently of another represent
H; F; Cl; Br; $CF_3$; CN; OH; $OCF_3$; $NH_2$; $C_{1-4}$-aliphatic residue, O—$C_{1-4}$-aliphatic residue, $N(H)C_{1-4}$-aliphatic residue, $N(C_{1-4}$-aliphatic residue$)_2$,
wherein the $C_{1-4}$-aliphatic residue in each case is saturated or unsaturated, branched or unbranched, unsubstituted or mono- or poly-substituted by one or more substituents each selected independently of one another from the group consisting of F, Cl, Br, I, O—$C_{1-4}$-aliphatic residue, OH and $OCF_3$;
$C_{3-10}$-cycloaliphatic residue or 3 to 10 membered heterocycloaliphatic residue, in each case saturated or unsaturated, unsubstituted or mono- or poly-substituted by one or more substituents each selected independently of one another from the group consisting of F, Cl, Br, $C_{1-4}$-aliphatic residue, OH, =O, O—$C_{1-4}$-aliphatic residue, $OCF_3$, $NH_2$, $N(H)C_{1-4}$-aliphatic residue and $N(C_{1-4}$-aliphatic residue$)_2$;
m represents 0, 1, 2 or 3;
Y represents O or $NR^{15}$,
wherein $R^{15}$ represents H or
$C_{1-4}$-aliphatic residue, saturated or unsaturated, branched or unbranched, unsubstituted or mono- or poly-substituted by one or more substituents each selected independently of one another from the group consisting of F, Cl, Br, $C_{1-4}$-aliphatic residue, OH, O—$C_{1-4}$-aliphatic residue, $OCF_3$, $NH_2$, $N(H)C_{1-4}$-aliphatic residue and $N(C_{1-4}$-aliphatic residue$)_2$; or
$C_{3-10}$-cycloaliphatic residue, saturated or unsaturated, unsubstituted or mono- or poly-substituted by one or more substituents each selected independently of one another from the group consisting of F, Cl, Br, $C_{1-4}$-aliphatic residue, OH, O—$C_{1-4}$-aliphatic residue, $OCF_3$, $NH_2$, $N(H)C_{1-4}$-aliphatic residue and $N(C_{1-4}$-aliphatic residue$)_2$;
o represents 0 or 1,
B represents $C_{1-8}$-aliphatic residue, saturated or unsaturated, branched or unbranched, unsubstituted or mono- or poly-substituted by one or more substituents each selected independently of one another from the group consisting of F, Cl, Br, CN, OH, =O, O—$C_{1-4}$-aliphatic residue, $OCF_3$, C(=O)OH, $CF_3$, $NH_2$, $NH(C_{1-4}$-aliphatic residue) and $N(C_{1-4}$-aliphatic residue$)_2$; or $C_{3-10}$-cycloaliphatic residue or 3 to 10 membered heterocycloaliphatic residue, in each case saturated or unsaturated, unsubstituted or mono- or poly-substituted by one or more substituents each selected independently of one another from the group consisting of F, Cl, Br, CN, OH, O—$C_{1-4}$-aliphatic residue, $OCF_3$, $C_{1-4}$-aliphatic residue, $OO_2H$, $CF_3$, $NH_2$, $NH(C_{1-4}$-aliphatic residue), $N(C_{1-4}$-aliphatic residue$)_2$ or $SCF_3$;
or
aryl or heteroaryl, in each case unsubstituted or mono- or poly-substituted by one or more substituents each selected independently of one another from the group consisting of F, Cl, Br, $NO_2$, CN, OH, O—$C_{1-4}$-aliphatic residue, $OCF_3$, $C_{1-4}$-aliphatic residue, $CO_2H$, $CF_3$, $NH_2$, $NH(C_{1-4}$-aliphatic residue), $N(C_{1-4}$-aliphatic residue$)_2$, S—$C_{1-4}$-aliphatic residue, $SCF_3$, phenyl, pyridyl and thienyl,
wherein benzyl, phenyl, pyridyl, thienyl can in each case be unsubstituted or mono- or poly-substituted by one or more substituents selected independently of one another from the group consisting of F, Cl, Br, $NO_2$, CN, OH, O—$C_{1-4}$-aliphatic residue, $OCF_3$, $C_{1-4}$-aliphatic residue, $CO_2H$, $CF_3$, $NH_2$, $NH(C_{1-4}$-aliphatic residue), $N(C_{1-4}$-aliphatic residue$)_2$, S—$C_{1-4}$-aliphatic residue and $SCF_3$.

Preferably,
$R^{14a}$ and $R^{14b}$ each independently of another represent
H; F; Cl; Br; $CF_3$; CN; OH; $OCF_3$; $NH_2$; $C_{1-4}$-aliphatic residue, O—$C_{1-4}$-aliphatic residue, $N(H)C_{1-4}$-aliphatic residue, $N(C_{1-4}$-aliphatic residue$)_2$,
wherein the $C_{1-4}$-aliphatic residue in each case is saturated or unsaturated, branched or unbranched, unsubstituted or mono- or poly-substituted by one or more substituents each selected independently of one another from the group consisting of F, Cl, Br, O—$C_{1-4}$-aliphatic residue and OH;
$C_{3-10}$-cycloaliphatic residue, saturated or unsaturated, unsubstituted or mono- or poly-substituted by one or more substituents each selected independently of one another from the group consisting of F, Cl, Br, $C_{1-4}$-aliphatic residue, OH and O—$C_{1-4}$-aliphatic residue;
m represents 0, 1, 2 or 3;
Y represents O or $NR^{15}$;
wherein $R^{15}$ represents H; or
$C_{1-4}$-aliphatic residue, saturated or unsaturated, unsubstituted; or
$C_{3-10}$-cycloaliphatic residue, saturated or unsaturated, unsubstituted;
o represents 0 or 1;
B represents
$C_{1-8}$-aliphatic residue, saturated or unsaturated, branched or unbranched, unsubstituted or mono- or poly-substituted by one or more substituents each selected independently of one another from the group consisting of F, Cl, CN, OH, O—$C_{1-4}$-aliphatic residue, $OCF_3$, $CF_3$, $NH_2$, $NH(C_{1-4}$-aliphatic residue), $N(C_{1-4}$-aliphatic residue$)_2$;
or
$C_{3-10}$-cycloaliphatic residue or 3 to 7 membered heterocycloaliphatic residue, in each case saturated or unsaturated, unsubstituted or mono- or poly-substituted by one or more substituents each selected independently of one another from the group consisting of F, Cl, CN, OH, O—$C_{1-4}$-aliphatic residue, $OCF_3$, $C_{1-4}$-aliphatic residue, $CF_3$, $NH_2$, $NH(C_{1-4}$-aliphatic residue) and $N(C_{1-4}$-aliphatic residue$)_2$; or
aryl or heteroaryl, in each case unsubstituted or mono- or poly-substituted by one or more substituents each selected independently of one another from the group consisting of F, Cl, CN, OH, O—$C_{1-4}$-aliphatic residue, $OCF_3$, $C_{1-4}$-aliphatic residue, $CF_3$, $NH_2$, $NH(C_{1-4}$-aliphatic residue) and $N(C_{1-4}$-aliphatic residue$)_2$.

Particularly preferably,
$R^{14a}$ and $R^{14b}$ each independently of the other represents H; F; Cl; $CF_3$; CN; $CH_3$; $CH_2CH_3$; $(CH_2)_2CH_3$; $CH(CH_3)_2$; cyclopropyl; $(CH_2)_3CH_3$; $CH(CH_3)CH_2CH_3$; $C(CH_3)_3$; $CH_2CF_3$; OH; $OCH_3$; $OCH_2CH_3$; $O(CH_2)_2OCH_3$ or $O(CH_2)_2OH$; $OCF_3$; $NH_2$; $N(H)CH_3$; $N(OH_3)_2$; $N(H)CH_2CH_3$; $N(CH_2CH_3)_2$; or $N(CH_3)(CH_2CH_3)$;
m represents 0, 1 or 2;
o represents 0; and
B represents
$C_{1-4}$-aliphatic residue, saturated, branched or unbranched, unsubstituted or mono- or poly-substituted by one or more substituents each selected independently of one another from the group consisting of F, Cl, OH, O—$C_{1-4}$-aliphatic residue, $OCF_3$ and $CF_3$;

$C_{3-10}$-cycloaliphatic residue, saturated, unsubstituted; or phenyl, naphthyl, pyridyl, thienyl, in each case unsubstituted or mono- or di- or tri-substituted by one, two or three substituents each selected independently of one another from the group consisting of F, Cl, CN, OH, O—$C_{1-4}$-aliphatic residue, $OCF_3$, $C_{1-4}$-aliphatic residue, $CF_3$, $NH_2$, $NH(C_{1-4}$-aliphatic residue) and $N(C_{1-4}$-aliphatic residue)$_2$.

Most particularly preferably, $R^{14a}$ and $R^{14b}$ each independently of another represent H; F; Cl; $CH_3$; $CH_2CH_3$; $(CH_2)_2CH_3$; $CH(CH_3)_2$; $(CH_2)_3CH_3$; $CH(CH_3)CH_2CH_3$; $C(CH_3)_3$; OH; $OCH_3$; $OCH_2CH_3$; $O(CH_2)_2OCH_3$ or $O(CH_2)_2OH$;

m represents 0, 1 or 2;

o represents 0; and

B represents $CH_3$; $CH_2CH_3$; $(CH_2)_2CH_3$; $CH(CH_3)_2$; $(CH_2)_3CH_3$; $CH(CH_3)CH_2CH_3$; $C(CH_3)_3$; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl or thienyl, in each case unsubstituted or mono-, di- or tri-substituted by one, two or three substituents each selected independently of one another from the group consisting of F, Cl, CN, OH, O—$C_{1-4}$-aliphatic residue, $OCF_3$, $C_{1-4}$-aliphatic residue, $CF_3$, $NH_2$, $NH(C_{1-4}$-aliphatic residue) and $N(C_{1-4}$-aliphatic residue)$_2$.

For o=0, the partial structure (T-1) for $R^1$ yields the partial structure (T1-1):

$$\text{(T1-1)} \quad -\!\!\!\!\!\{-(CR^{14a}R^{14b})_m-B,$$

In a preferred embodiment for n=0, $R^{14a}$ and $R^{14b}$ each independently of the other represents H; F; Cl; $CH_3$; $CH_2CH_3$; $(CH_2)_2CH_3$; $CH(CH_3)_2$; $(CH_2)_3CH_3$; $CH(CH_3)CH_2CH_3$; $C(CH_3)_3$; OH; $OCH_3$; $OCH_2CH_3$; $O(CH_2)_2OCH_3$; or $O(CH_2)_2OH$.

In a preferred embodiment for m=0, 1 or 2, particularly preferred for m=0, B represents phenyl, pyridyl or thienyl, mono- or di- or tri-substituted by one, two or three substituents each selected independently of one another from the group consisting of F, Cl, CN, OH, O—$C_{1-4}$-aliphatic residue, $OCF_3$, $C_{1-4}$-aliphatic residue, $CF_3$, $NH_2$, $NH(C_{1-4}$-aliphatic residue) and $N(C_{1-4}$-aliphatic residue)$_2$.

In a preferred embodiment for m=1 or 2, B represents cyclopropyl; cyclobutyl; cyclopentyl; cyclohexyl; cycloheptyl; adamantyl; bicyclo[2.2.1]heptyl or bicyclo[2.2.2]octyl.

In a preferred embodiment for m=0, 1 or 2, B represents $CH_3$; $CH_2CH_3$; $(CH_2)_2CH_3$; $CH(CH_3)_2$; $(CH_2)_3CH_3$; $CH(CH_3)CH_2CH_3$ or $C(CH_3)_3$.

A further particularly preferred embodiment of the invention, the compound of the general formula (I) has the general formula (II):

(II)

In a further embodiment of the invention, each radical $R^7$, independently of another, represents H, F; Cl; CN; $CF_3$; $CHF_2$; $CH_2F$; $OCF_3$; $OCHF_2$; $OCH_2F$; $SCF_3$; O—$C_{1-4}$-aliphatic residue, $C_{1-4}$-aliphatic residue or $S(=O)_2$—$C_{1-4}$-aliphatic residue, wherein the $C_{1-4}$-aliphatic residue in each case may be unsubstituted or mono- or polysubstituted with at least one substituent selected from the group consisting of F, Cl, OH, $OCF_3$, $CF_3$ and O—$C_{1-4}$-aliphatic residue.

Preferably, each radical $R^7$, independently of another, represents

H, F; Cl; CN; $CF_3$; $CHF_2$; $CH_2F$; $OCF_3$; $OCHF_2$; $OCH_2F$; $SCF_3$; $CH_3$; $CH_2CH_3$; $(CH_2)_2CH_3$; $CH(CH_3)_2$; $(CH_2)_3CH_3$, $CH(CH_3)CH_2CH_3$; $C(CH_3)$; $CH_2CF_3$; $OCH_3$; $OCH_2CH_3$; $O(CH_2)_2CH_3$; $OCH(CH_3)_2$; $O(CH_2)_3CH_3$; $OCH(CH_3)CH_2CH_3$; $OC(CH_3)$; $O(CH_2)_2OCH_3$; $O(CH_2)_2OH$; $S(=O)_2CH_3 S(=O)_2CH_2CH_3$, $S(=O)_2CH(CH_3)_2$ or $S(=O)_2CH_2CH_2CH_3$;

Particularly preferably, each radical $R^7$, independently of another, represents H, F; Cl; CN; $CF_3$; $OCF_3$; $CH_3$; $CH_2CH_3$; $CH(CH_3)_2$ or $OCH_3$.

Most preferably, each radical $R^7$, independently of another, represents

H; F; Cl; $CH_3$; $CH_2CH_3$; $OCH_3$ or $CF_3$; in particular H.

In a further embodiment of the invention, $R^8$ represents H or $C_{1-4}$-aliphatic residue, wherein the $C_{1-4}$-aliphatic residue may be unsubstituted or mono- or polysubstituted with at least one substituent selected from the group consisting of F, Cl, Br, I, OH, $OCF_3$, $CF_3$ and O—$C_{1-4}$-aliphatic residue.

Preferably, $R^8$ represents H; $CH_3$; $CH_2CH_3$; $CH(CH_3)_2$ or $CF_3$.

Particularly preferably, $R^8$ represents H or $CH_3$ or $CH_2CH_3$ or $CH(CH_3)_2$.

Most preferably, $R^8$ represents H or $CH_3$.

In a further preferred embodiment, the radicals $R^2$, $R^3$, $R^4$; $R^5$; $R^{10}$, $R^{11}$, $R^{12}$ and $R^{13}$ each independently of another represent H; F; Cl; Br; I; $NO_2$; $CF_3$; CN; OH; $OCF_3$; SH; $SCF_3$; $C_{1-4}$-aliphatic residue; O—$C_{1-4}$-aliphatic residue or S—$C_{1-4}$-aliphatic residue, wherein the $C_{1-4}$-aliphatic residue in each case may be saturated or unsaturated, branched or unbranched, unsubstituted or mono- or poly-substituted by one or more substituents each selected independently of one another from the group consisting of F, Cl, Br, I, OH and O—$C_{1-4}$-aliphatic residue; or $C_{3-6}$-cycloaliphatic residue, saturated or unsaturated, branched or unbranched, unsubstituted or mono- or poly-substituted by one or more substituents each selected independently of one another from the group consisting of F, Cl, Br, I, OH, =O and O—$C_{1-4}$-aliphatic residue;

or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{12}$ and $R^{13}$, together with the carbon atom(s) joining them, form a cyclopropyl, cyclobutyl, cyclopentyl, cyclohexyl, pyrrolidinyl or piperidinyl, in each case unsubstituted or mono- or poly-substituted by one or more substituents each selected independently of another from the group consisting of F, Cl, Br, I, OH, =O and O—$C_{1-4}$-aliphatic residue; wherein the remaining substituents $R^2$, $R^3$; $R^4$; $R^5$; $R^{10}$, $R^{11}$, $R^{12}$ and $R^{13}$ in each case have the meaning given above.

Preferably, the radicals $R^2$, $R^3$; $R^4$; $R^5$; $R^{10}$, $R^{11}$, $R^{12}$ and $R^{13}$ each independently of the others represents H; F; Cl; $CF_3$; CN; OH; $OCF_3$; $SCF_3$; $CH_3$; $CH_2CH_3$; $(CH_2)_2CH_3$; $CH(CH_3)_2$; $(CH_2)_3CH_3$; $CH(CH)_3CH_2CH_3$; $C(CH_3)_3$; $OCH_3$; $OCH_2CH_3$; $O(CH_2)_2OCH_3$; $O(CH_2)_2OH$; $SCH_3$; $SCH_2CH_3$; cyclopropyl; cyclobutyl; cyclopentyl; cyclohexyl;

or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{11}$ and $R^{13}$, together with the carbon atom(s) joining them, form a cyclopropyl, cyclobutyl, cyclopentyl or cyclohexyl, in each case unsubstituted; wherein the remaining substituents $R^2$, $R^3$; $R^4$; $R^5$; $R^{10}$, $R^{11}$, $R^{12}$ and $R^{13}$ in each case have the meaning given above.

Particularly preferably, the radicals $R^2$, $R^3$, $R^4$, $R^5$, $R^{10}$, $R^{11}$, $R^{12}$ and $R^{13}$ each independently of another represent H; F; Cl; CN; $CF_3$; $OCF_3$; $SCF_3$; $CH_3$; $CH_2CH_3$; $(CH_2)_2CH_3$; $CH(CH_3)_2$; cyclopropyl; $OCH_3$; $SCH_3$; or $R^2$ and $R^4$ form a cyclopropyl, cyclobutyl, cyclopentyl or cyclohexyl ring substituted as desired by H, F, Cl, $CH_3$, $CH_2CH_3$, $OCH_3$, preferably an unsubstituted cyclopentyl or cyclohexyl ring.

Most preferably, the radicals $R^2$, $R^3$, $R^4$, $R^5$, $R^{10}$, $R^{11}$, $R^{12}$ and $R^{13}$ each independently of another represent H; F; Cl; $CH_3$; $CH_2CH_3$; $(CH_2)_2CH_3$; $CH(CH_3)_2$; cyclopropyl; in particular H; F; $CH_3$ or $CH_2CH_3$.

In a particularly preferred embodiment of the invention, the compound according to formula (I) is characterized in that the radicals $R^2$, $R^3$, $R^4$ and $R^5$ each represent H.

In another particularly preferred embodiment of the invention, the compound according to formula (I) is characterized in that
the radicals $R^2$, $R^3$, $R^4$ and $R^5$ each represent H and
the radicals $R^{12}$ and $R^{13}$ each represent H.

In another particularly preferred embodiment of the invention, the compound according to formula (I) is characterized in that
the radicals $R^2$, $R^3$, $R^4$ and $R^5$ each represent H and
the radicals $R^{12}$ and $R^{13}$ each represent F.

In a particularly preferred embodiment of the invention, the compound according to formula (I) is characterized in that the radicals $R^{12}$ and $R^{13}$ each independently of another represent H, F or $CH_3$.

More preferably, the radicals $R^{12}$ and $R^{13}$ each independently of another represent H or F.

In a further preferred embodiment of the invention,
the radical $R^6$ represents
$C_{3-10}$-cycloaliphatic residue or 3 to 10 membered heterocycloaliphatic residue,
in each case saturated or unsaturated, unsubstituted or mono- or poly-substituted by one or more substituents each selected independently of one another from the group consisting of F, Cl, Br, I, $NO_2$, CN, OH, =O, O—$C_{1-4}$-aliphatic residue, $OCF_3$, $C_{1-4}$-aliphatic residue, $CF_3$, SH, S—$C_{1-4}$-aliphatic residue and $SCF_3$; or aryl or heteroaryl, in each case unsubstituted or mono- or poly-substituted by one or more substituents each selected independently of one another from the group consisting of F, Cl, Br, I, $NO_2$, CN, OH, O—$C_{1-4}$-aliphatic residue, $OCF_3$, $C_{1-4}$-aliphatic residue, $CF_3$, $NH_2$, $NH(C_{1-4}$-aliphatic residue), $N(C_{1-4}$-aliphatic residue$)_2$, SH, S—$C_{1-4}$-aliphatic residue and $SCF_3$.

Preferably,
$R^6$ represents
$C_{3-6}$-cycloaliphatic residue, saturated or unsaturated; or pyrrolidinyl, piperazinyl, 4-methylpiperazinyl, piperidinyl, morpholinyl,
in each case unsubstituted or mono- or poly-substituted by one or more substituents each selected independently of one another from the group consisting of F, Cl, Br, I, OH, O—$C_{1-4}$-aliphatic residue, $OCF_3$, $C_{1-4}$-aliphatic residue, $CF_3$, SH, S—$C_{1-4}$-aliphatic residue and $SCF_3$; or
phenyl, naphthyl, pyridyl or thienyl,
in each case unsubstituted or mono- or poly-substituted by one or more substituents each selected independently of one another from the group consisting of F, Cl, Br, I, CN, OH, O—$C_{1-4}$-aliphatic residue, $OCF_3$, $C_{1-4}$-aliphatic residue, $CF_3$, SH, S—$C_{1-4}$-aliphatic residue and $SCF_3$.

In a particularly preferred embodiment of the invention, the radical $R^6$ is selected from the group consisting of phenyl, pyridyl or thienyl,
in each case unsubstituted or mono- or poly-substituted by one or more substituents each selected independently of one another from the group consisting of F, Cl, Br, CN, OH, O—$C_{1-4}$-aliphatic residue, $OCF_3$, $C_{1-4}$-aliphatic residue, $CF_3$ and $SCF_3$.

In most particularly preferred embodiment of the invention,
$R^6$ represents phenyl, pyridyl and thienyl, in each unsubstituted or mono- or poly-substituted by one or more substituents each independently selected from the group consisting of F, Cl, Br, CN, $CH_3$; $CH_2CH_3$; $(CH_2)_2CH_3$; $CH(CH_3)_2$; $(CH_2)_3CH_3$; $CH(CH)_3CH_2CH_3$; $C(CH_3)_3$; $OCH_3$; $OCH_2CH_3$; OH, $OCF_3$, $CF_3$, and $SCF_3$.

In a further, particularly preferred embodiment of the invention, the compound according to formula (I) is characterized in that
$A^1$ represents S;
$A^2$ represents $S(=O)_2$ or $CR^{12}R^{13}$,
wherein $R^{12}$ and $R^{13}$ both represent H or both represent F;
$R^1$ represents the partial structure (T1-1)

(T1-1)

wherein
$R^{14a}$ and $R^{14b}$ each independently of the other represents H; F; Cl; $CH_3$; $CH_2CH_3$; $(CH_2)_2CH_3$; $CH(CH_3)_2$; $(CH_2)_3CH_3$; $CH(CH)_3CH_2CH_3$; $C(CH_3)_3$; OH; $OCH_3$; $OCH_2CH_3$; $O(CH_2)_2OCH_3$; or $O(CH_2)_2OH$;
m represents 0, 1 or 2 and
B represents phenyl or naphthyl or pyridyl or thienyl, in each case unsubstituted or mono- or di- or tri-substituted by one, two or three substituents each selected independently of one another from the group consisting of F, Cl, CN, OH, O-$_{1-4}$-aliphatic residue, $OCF_3$, $C_{1-4}$-aliphatic residue, C(=O)—OH, $CF_3$, $NH_2$, $NH(C_{1-4}$-aliphatic residue) and $N(C_{1-4}$-aliphatic residue$)_2$;

$R^2$, $R^3$, $R^4$, $R^5$, $R^{10}$, $R^{11}$, $R^{12}$ and $R^{13}$
 each independently of the others represent H; F; Cl; Br; I; $NO_2$; $CF_3$; CN; OH; $OCF_3$; SH; $SCF_3$; $CH_3$; $CH_2CH_3$; $CH_2CH_2CH_3$; $CH(CH_3)_2$; $CH_2CH_2CH_2CH_3$; $CH(CH_3)_3CH_2CH_3$; $CH_2CH(CH_3)_2$; $C(CH_3)_3$; $OCH_3$; $OCH_2CH_3$; $O(CH_2)_2OCH_3$; $O(CH_2)_2OH$; $SCH_3$; $SCH_2CH_3$; cyclopropyl; cyclobutyl; cyclopentyl; cyclohexyl;
or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{12}$ and $R^{13}$, together with the carbon atom(s) joining them, form a cyclopropyl, cyclobutyl, cyclopentyl or cyclohexyl, in each case unsubstituted;
 wherein the remaining substituents $R^2$, $R^3$; $R^4$; $R^5$; $R^{10}$, $R^{11}$, $R^{12}$ and $R^{13}$ in each case have the meaning given above;

$R^6$ represents phenyl,
 unsubstituted or mono- or poly-substituted by one or more substituents each selected independently of one another from the group consisting of F, Cl, Br, I, CN, OH, $OCH_3$, $OCH_2CH_3$, $OCF_3$, $CH_3$, $CH_2CH_3$, $CH(CH_3)_2$ and $CF_3$;

each $R^7$ represents H, F; Cl; CN; $CF_3$; $CHF_2$; $CH_2F$; $OCF_3$; $OCHF_2$; $OCH_2F$; $SCF_3$; $CH_3$; $CH_2CH_3$; $CH_2CH_2CH_3$; $CH(CH_3)_2$; $CH_2CH_2CH_2CH_3$; $CH(CH_3)_3CH_2CH_3$; $CH_2CH(CH_3)_2$; $C(CH_3)_3$; $OCH_3$; $OCH_2CH_3$; $O(CH_2)_2OCH_3$; $O(CH_2)_2OH$; $S(=O)_2CH_3 S(=O)_2CH_2CH_3$, $S(=O)_2CH(CH_3)_2$ or $S(=O)_2CH_2CH_2CH_3$; and $R^8$ represents H or $CH_3$ or $CH_2CH_3$ or $CH(CH_3)_2$.

In another preferred embodiment of the invention, the compound according to formula (I) is selected from the group consisting of 1  2-[[3,3-Difluoro-3-(4-fluorophenyl)-propyl]sulfanyl]-N-(3-methyl-butyl)-benzamide,
2  N-(3,3-Dimethyl-butyl)-2-[3-(4-fluorophenyl)-propylsulfanyl]-benzamide,
3  3-[[3,3-Difluoro-3-(4-fluorophenyl)-propyl]sulfanyl]-N-(3-methyl-butyl)-pyridine-2-carboxylic acid amide,
4  3-[2-(Benzenesulfonyl)-ethylsulfanyl]-N-(thiophen-2-ylmethyl)-pyridine-2-carboxylic acid amide,
5  4-[[3,3-Difluoro-3-(4-fluorophenyl)-propyl]sulfanyl]-N-(3-methyl-butyl)-pyridine-3-carboxylic acid amide,
6  4-[[3,3-Difluoro-3-(4-fluorophenyl)-propyl]sulfanyl]-N-[(4-fluorophenyl)-methyl]-pyridine-3-carboxylic acid amide,
7  3-[[3,3-Difluoro-3-(4-fluorophenyl)-propyl]sulfanyl]-N-(3-methyl-butyl)-pyridine-4-carboxylic acid amide,
8  3-[2-(Benzenesulfonyl)-ethylsulfanyl]-N-(thiophen-2-ylmethyl)-pyridine-4-carboxylic acid amide,
9  3-[[3,3-Difluoro-3-(4-fluorophenyl)-propyl]sulfanyl]-N-(3-methyl-butyl)-pyrazine-2-carboxylic acid amide,
10  4-[[3,3-Difluoro-3-(4-fluorophenyl)-propyl]sulfanyl]-N-(3-methyl-butyl)-pyrimidine-5-carboxylic acid amide,
11  4-[[3,3-Difluoro-3-(4-fluorophenyl)-propyl]sulfanyl]-N-[(4-fluorophenyl)-methyl]-pyrimidine-5-carboxylic acid amide,
12  3-[[3,3-Difluoro-3-(4-fluorophenyl)-propyl]sulfanyl]-N-(3-methyl-butyl)-pyridazine-4-carboxylic acid amide,
13  3-[[3,3-Difluoro-3-(4-fluorophenyl)-propyl]sulfanyl]-N-[(4-fluorophenyl)-methyl]-pyridazine-4-carboxylic acid amide,
14  4-[[3,3-Difluoro-3-(4-fluorophenyl)-propyl]sulfanyl]-N-[(4-fluorophenyl)-methyl]-thiazole-5-carboxylic acid amide,
15  4-[[3,3-Difluoro-3-(4-fluorophenyl)-propyl]sulfanyl]-N-[(4-fluorophenyl)-methyl]-2-methyl-thiazole-5-carboxylic acid amide,
or physiologically acceptable salts thereof.

The specific carboxamides according to the invention and in each case the corresponding acids, bases, salts and solvates are suitable as pharmaceutical active ingredients in medicaments.

In another aspect, the invention therefore further provides a medicament comprising at least one carboxamide of the general formula (I) according to the invention wherein the radicals $R^1$ to $R^{14}$ have the meaning given above and, optionally, one or more pharmaceutically acceptable auxiliary substances.

In addition to at least one compound according to the invention, the medicaments according to the invention optionally comprise suitable additives and/or auxiliary substances, that is to say also carriers, fillers, solvents, diluents, colorings and/or binders, and can be administered as liquid medicament forms in the form of injection solutions, drops or juices, as semi-solid medicament forms in the form of granules, tablets, pellets, patches, capsules, plasters/spray-on plasters or aerosols. The choice of auxiliary substances etc. and the amounts thereof to be used are dependent on whether the medicament is to be administered orally, perorally, parenterally, intravenously, intraperitoneally, intradermally, intramuscularly, intranasally, buccally, rectally or locally, for example to the skin, the mucosa or into the eyes. Preparations in the form of tablets, dragées, capsules, granules, drops, juices and syrups are suitable for oral administration, and solutions, suspensions, readily reconstitutable dry preparations and sprays are suitable for parenteral, topical and inhalatory administration. Compounds according to the invention in a depot, in dissolved form or in a plaster, optionally with the addition of agents that promote penetration through the skin, are suitable percutaneous forms of administration. Forms of preparation for administration orally or percutaneously can release the compounds according to the invention in a delayed manner. The compounds according to the invention can also be administered in parenteral long-term depot forms such as, for example, implants or implanted pumps. In principle, other further active ingredients known to the person skilled in the art can be added to the medicaments according to the invention.

The medicaments according to the invention are suitable for influencing KCNQ2/3 channels and exert an agonistic or antagonistic action, in particular an agonistic action.

The medicaments according to the invention are preferably suitable for the treatment of disorders or diseases that are mediated at least in part by KCNQ2/3 channels.

The medicaments according to the invention are suitable preferably for the treatment of one or more diseases selected from the group consisting of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

The medicaments according to the invention are suitable particularly preferably for the treatment of pain, most particularly preferably of chronic pain, neuropathic pain, inflammatory pain and muscular pain.

The medicaments according to the invention are also particularly preferably suitable for the treatment of epilepsy.

In another aspect of the invention, the invention further provides the use of at least one carboxamide according to the invention, and optionally one or more pharmaceutically acceptable auxiliary substances, in the preparation of a medicament for the treatment of disorders or diseases that are mediated at least in part by KCNQ2/3 channels.

Preference is given to the use of at least one carboxamide according to the invention, and optionally one or more pharmaceutically acceptable auxiliary substances, in the preparation of a medicament for the treatment of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

Particular preference is given to the use of at least one carboxamide according to the invention, and optionally one or more pharmaceutically acceptable auxiliary substances, in the preparation of a medicament for the treatment of pain, most particularly preferably chronic pain, neuropathic pain, inflammatory pain and muscular pain.

Particular preference is given also to the use of at least one carboxamide according to the invention, and optionally one or more pharmaceutically acceptable auxiliary substances, in the preparation of a medicament for the treatment of epilepsy.

In another aspect of the invention, the invention further provides at least one carboxamide according to the invention, and optionally one or more pharmaceutically acceptable auxiliary substances, for the treatment of disorders or diseases that are mediated at least in part by KCNQ2/3 channels.

In another aspect of the invention, the invention further provides at least one carboxamide according to the invention, and optionally one or more pharmaceutically acceptable auxiliary substances, for the treatment of pain, especially pain selected from the group consisting of acute pain, chronic pain, neuropathic pain, muscular pain and inflammatory pain; epilepsy, urinary incontinence, anxiety, dependency, mania, bipolar disorders, migraine, cognitive diseases, dystonia-associated dyskinesias and/or urinary incontinence.

Particular preference is given to at least one carboxamide according to the invention, and optionally one or more pharmaceutically acceptable auxiliary substances, for the treatment of pain, most particularly preferably of chronic pain, neuropathic pain, inflammatory pain and muscular pain.

Particular preference is given also to at least one carboxamide according to the invention, and optionally one or more pharmaceutically acceptable auxiliary substances, for the treatment of epilepsy.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363). The effectiveness against epilepsy can be demonstrated, for example, in the DBA/2 mouse model (De Sarro et al., Naunyn-Schmiedeberg's Arch. Pharmacol. 2001, 363, 330-336).

The specific carboxamides according to the invention preferably have an $EC_{50}$ value of not more than 5 µM or not more than 3 µM, more preferably not more than 2 µM or not more than 1 µM, yet more preferably not more than 0.9 µM or not more than 0.6 µM, most preferably not more than 0.5 µM or not more than 0.3 µM and especially not more than 0.2 µM or not more than 0.1 µM. Methods for determining the $EC_{50}$ value are known to the person skilled in the art. The $EC_{50}$ value is preferably determined by fluorimetry, particularly preferably as described under "Pharmacological Experiments".

In another aspect of the invention, the invention further provides processes for the preparation of the carboxamides according to the invention.

The term "compounds according to the invention" or "carboxamides according to the invention" in foregoing aspects of the invention encompasses all possible stereoisomers and tautomers as well as the respective corresponding acids, bases, salts and solvates.

The embodiments and in particular the preferred embodiments of any aspect of the present invention apply to all other aspects of the inventions respectively.

The chemicals and reaction components used in the reactions described hereinbelow are available commercially or can in each case be prepared by conventional methods known to the person skilled in the art.

General Reaction Schemes

General reaction scheme I (synthesis of precursors SM01 and SM02):

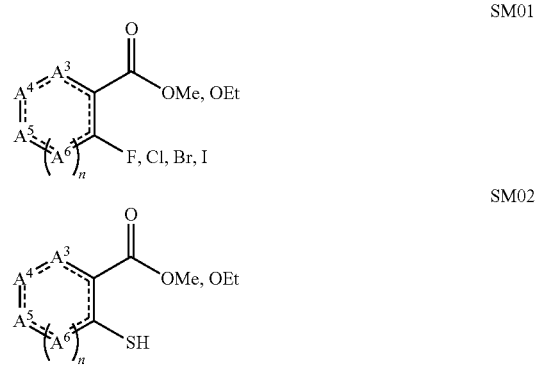

A plurality of syntheses of and synthesis paths to compounds of the general formulae SM01 and SM02 with a very broad substitution pattern for residues $A^3$ to $A^6$ are known in the current specialist literature. Previously unknown intermediates of the general formulas SM01 and SM02 with similar substitution patterns for residues $A^3$ to $A^6$ as outlined thereafter and whose syntheses are not described in greater detail can be produced by the person skilled in the art according to these known methods or by combination of the known methods.

General reaction scheme II:

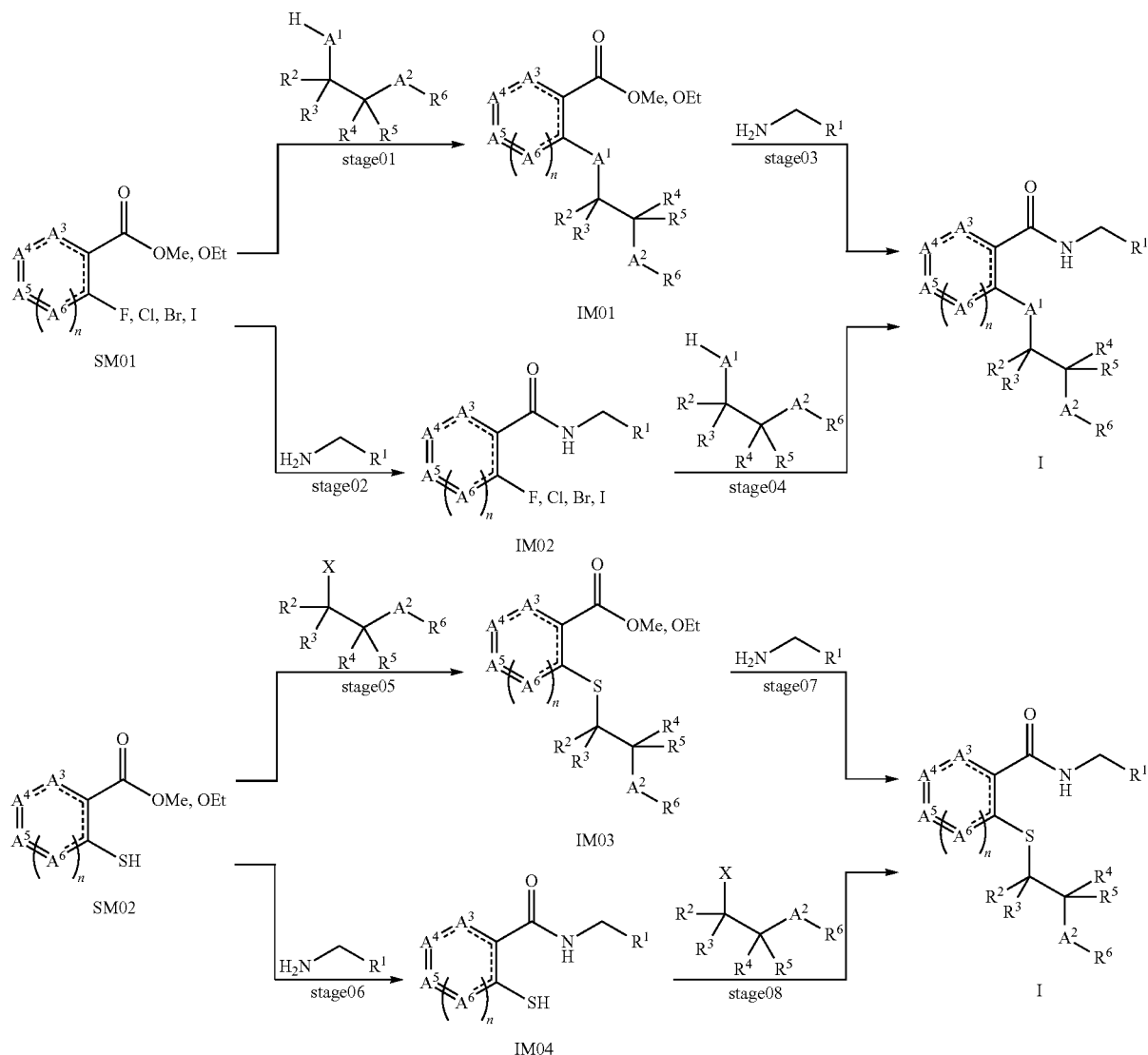

In stage01 and stage04, haloarenes of the general formulae SM01 and IM02 can be converted to yield compounds of the general formulae IM01 and I with compounds of the general formula R$^6$-A$^2$-(CR$^4$R$^5$)—(CR$^2$R$^3$)-A$^1$-H according to methods known to the person skilled in the art, example by treating with a suitable base, for example caesium carbonate.

In stage02, stage03, stage06, and stage07 esters of the general formulae SM01, IM01, SM02, and IM03 can be converted to yield amides of the general formulae IM02, IM04, and I with amines of the general formula R$^1$—CH$_2$—NH$_2$ according to methods known to the person skilled in the art, for example by the addition of trimethyl aluminium, or by ester hydrolysis to yield the corresponding carboxylic acid followed by reaction with amines of the general formula R$^1$—CH$_2$—NH$_2$ according to methods known to the person skilled in the art, for example using a suitable coupling reagent, for example O-(7-azabenzotriazol-1-yl)-N,N,N',N'-tetramethyluronium hexafluorophosphate.

In stage05 and stage08, thiols of the general formulae SM02 and IM04 can be converted to yield compounds of the general formulae IM03 and I (in which A$^1$ denotes sulphur) with compounds of the general formula R$^6$-A$^2$-(CR$^4$R$^5$)—(CR$^2$R$^3$)—X, in which X denotes halogen or a sulfonic acid ester, for example mesylate, according to methods known to the person skilled in the art, for example by treating with a suitable base, for example potassium carbonate.

Thus obtained compounds of the general formula I can be further transformed to introduce and/or exchange one or more of the substituents A$^1$; A$^2$; A$^3$, A$^4$, A$^5$, A$^6$, R$^1$; R$^2$, R$^3$, R$^4$, R$^5$, and R$^6$ by simple derivatization reactions known to the person skilled in the art, for example esterification, ester formation, amide formation, etherification, ether cleavage, oxidation, reduction, hydrogenation, substitution or cross-coupling reactions.

The invention will be described hereinafter with the aid of a number of examples. This description is intended merely by way of example and does not limit the general idea of the invention.

DESCRIPTION OF THE SYNTHESES

Abbreviations

AcOH acetic acid
aq. aqueous d days
DCM dichloromethane
DMF N,N-dimethylformamide
EtOAc ethyl acetate
EtOH ethanol
sat. saturated
h hour(s)
sol. solution
M mol/L
m/z mass-to-charge ratio
MeOH methanol
min minutes
MS mass spectrometry
RT room temperature 23±7° C.
THF tetrahydrofuran
TLC thin layer chromatography
v/v ratio by volume The yields of the compounds prepared were not optimized. All temperatures are uncorrected. All starting materials which are not explicitly described were either commercially available (the details of suppliers such as for example Acros, Avocado, Aldrich, Bachem, Fluka, Lancaster, Maybridge, Merck, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art. The mixing ratios of solvents or eluents for chromatography are specified in v/v.

All the intermediate products and exemplary compounds were analytically characterised by means of $^1$H-NMR spectroscopy. In addition, mass spectrometry tests (MS, m/z for [M+H]$^+$) were carried out for all the exemplary compounds and selected intermediate products.

Synthesis of Exemplary Compounds

Synthesis of Example 1

2-[[3,3-Difluoro-3-(4-fluorophenyl)-propyl]sulfanyl]-N-(3-methyl-butyl)-benzamide

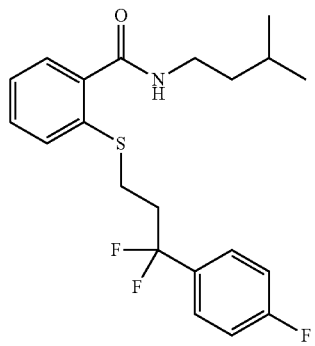 [SMILES: CC(C)CCNC(=O)c1ccccc1SCCC(F)(F)c1ccc(F)cc1]

a) Synthesis of acetic acid [3-(4-fluorophenyl)-3-oxo-propyl]ester

To a solution of 3-chloro-1-(4-fluorophenyl)-propan-1-one (4.0 g, 21.5 mmol) in AcOH (30 ml) in a sealed tube are added sodium acetate (8.64 g, 105.4 mmol) and potassium iodide (0.36 g, 2.15 mmol) at RT. The reaction mixture is stirred at 130° C. for 16 h. After completion of reaction, the mixture is diluted with water (60 ml) and neutralized with aqueous sodium carbonate at 0° C. The aqueous layer is extracted with DCM (3×100 ml). The combined organic layers are washed with water (200 ml), brine (200 ml), dried over anhydrous sodium sulfate and evaporated in vacuo to get the crude product, which is purified by column chromatography (silica gel, 10% EtOAc/hexane) to yield acetic acid [3-(4-fluorophenyl)-3-oxo-propyl]ester (3.00 g, 14.3 mmol, 66%).

b) Synthesis of acetic acid 2-[2-(4-fluorophenyl)[1,3]dithiolan-2-yl]ethyl ester To a solution of acetic acid [3-(4-fluorophenyl)-3-oxo-propyl]ester (2.0 g, 9.52 mmol) in dry dichloromethane (40 ml) are added 1,2-ethanedithiol (1.79 g, 19.0 mmol) and boron trifluoride diethyl ether complex (0.68 g, 4.76 mmol) at 0° C. The resulting reaction mixture is stirred at RT for 16 h. After completion of reaction, the mixture is neutralized with 10M aqueous sodium hydroxide and extracted with DCM (3×100 ml). The combined organic layers are washed with water (100 ml), brine (100 ml), dried over anhydrous sodium sulfate and evaporated in vacuo to get the crude, which is purified by column chromatography (silica gel, 5% ethyl acetate/hexane) to yield acetic acid 2-[2-(4-fluorophenyl)-[1,3]dithiolan-2-yl]-ethyl ester (1.80 g, 6.29 mmol, 66%).

c) Synthesis of acetic acid [3,3-difluoro-3-(4-fluorophenyl)-propyl]ester

To a solution of 1,3-Dibromo-5,5-dimethylhydantoin (5.96 g, 20.8 mmol) in dry DCM (25 ml) is added 30% hydrogen fluoride pyridine (21 ml) at −78° C. followed by the addition of acetic acid 2-[2-(4-fluorophenyl)-[1,3]dithiolan-2-yl]ethyl ester (1.50 g, 5.24 mmol) in dry DCM (25 ml) at the same temperature. The reaction mixture is stirred at −78° C. for 1.5 h and then allowed to warm to RT over a period of 1 h. The reaction mixture is stirred at RT for 1 h. After completion of reaction, the mixture is neutralized with saturated sodium hydrogen carbonate solution and the aqueous layer is extracted with DCM (3×60 ml). The organic layer is washed with 20% hydrochloric acid (50 ml), water (120 ml), brine (120 ml), dried over anhydrous sodium sulfate and evaporated in vacuo to yield acetic acid [3,3-difluoro-3-(4-fluorophenyl)-propyl]ester (1.10 g, 4.74 mmol, 90%), which is used in the next step without further purification.

d) Synthesis of 3,3-difluoro-3-(4-fluorophenyl)-propan-1-ol

To a solution of acetic acid [3,3-difluoro-3-(4-fluorophenyl)-propyl]ester (5.50 g, 23.7 mmol) in ethanol (70 ml) is added 35% aqueous sodium hydroxide (20 ml) at 0° C. and the reaction mixture is stirred at RT for 1 h. After completion of reaction, the solvent is evaporated and the residue is diluted with water (150 ml) and acidified with aqueous hydrochloric acid before extraction with EtOAc (3×100 ml). The combined organic layers are washed with water (150 ml), brine (150 ml), dried over anhydrous sodium sulfate and evaporated in vacuo to get the crude product, which is purified by column chromatography (silica gel, 10% EtOAc/hexane) to yield 3,3-difluoro-3-(4-fluorophenyl)-propan-1-ol (4.30 g, 22.6 mmol, 95%).

e) Synthesis of 1-(3-bromo-1,1-difluoro-propyl)-4-fluoro-benzene

To a stirred solution of 3,3-difluoro-3-(4-fluorophenyl)-propan-1-ol (5.10 g, 26.8 mmol) in dry DCM (50 ml) is added tetrabromomethane (16.0 g, 48.3 mmol) followed by addition of triphenylphosphine (12.6 g, 48.3 mmol) at 0° C. The reaction mixture is allowed to stir at RT for 1 h. After completion of reaction, the solvent is evaporated to get the crude product, which is purified by column chromatography (silica gel, 5% EtOAc/hexane) to yield compound I-(3-bromo-1,1-difluoro-propyl)-4-fluoro-benzene (4.80 g, 19.6 mmol, 71%).

f) Synthesis of 2-[[3,3-difluoro-3-(4-fluorophenyl)-propyl]sulfanyl]-benzoic acid To a solution of 2-mercapto-benzoic acid (0.10 g, 0.65 mmol) in acetone (30 ml) are added 1-(3-bromo-1,1-difluoro-propyl)-4-fluoro-benzene (0.16 g, 0.65 mmol) and potassium carbonate (0.27 g, 1.95 mmol) at RT. The reaction mixture is stirred at 70° C. for 2.5 h. The reaction mixture is diluted with water (20 ml), acidified with 2M hydrochloric acid and the aqueous layer is extracted with EtOAc (3×20 ml). The combined organic layers are washed with water (15 ml), brine (15 ml), dried over sodium sulfate and evaporated to dryness. The crude product is purified by column chromatography (silica gel, 80% EtOAc/hexane) to yield 2-[[3,3-difluoro-3-(4-fluorophenyl)-propyl]sulfanyl]-benzoic acid (0.08 g, 0.24 mmol, 37%).

g) Synthesis of 2-[[3,3-difluoro-3-(4-fluorophenyl)-propyl]sulfanyl]-N-(3-methyl-butyl)-benzamide To a stirred solution of 2-[[3,3-difluoro-3-(4-fluorophenyl)-propyl]sulfanyl]-benzoic acid (0.24 g, 0.73 mmol) in dry tetrahydrofuran (10 ml) are added O-(7-azabenzotriazol-1-yl)-N,N,N',N'-tetramethyluronium hexafluorophosphate (0.30 g, 0.80 mmol) and triethylamine (0.38 ml, 2.2 mmol) at RT. The reaction mixture is stirred for 5 min at RT followed by the addition of 3-methyl-butyl-amine (0.1 ml, 0.88 mmol). The reaction mixture is stirred at RT for 2 h. After completion of the reaction, the solvent is distilled off and the residue is diluted with saturated sodium hydrogen carbonate solution (20 ml) before extraction with EtOAc (3×30 ml). The organic layer is washed with saturated ammonium chloride solution (30 ml), water (30 ml), brine (30 ml), dried over anhydrous sodium sulfate and evaporated in vacuo to get the crude product, which is purified by column chromatography (silica gel, 50% EtOAc/hexane) to yield 2-[[3,3-difluoro-3-(4-fluorophenyl)-propyl]sulfanyl]-N-(3-methyl-butyl)-benzamide (example 1) (0.16 g, 0.41 mmol, 56%). [M+H]$^+$ 396.1.

Synthesis of Example 3

3-[[3,3-Difluoro-3-(4-fluorophenyl)-propyl]sulfanyl]-N-(3-methyl-butyl)-pyridine-2-carboxylic acid amide

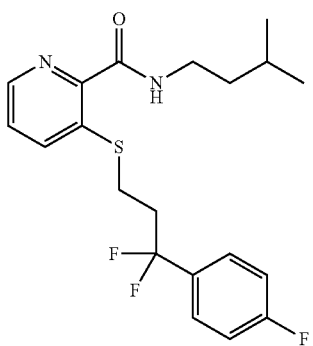 [SMILES: CC(C)CCNC(=O)c1ncccc1SCCC(F)(F)c1ccc(F)cc1]

a) Synthesis of ethanethioic acid S-[3,3-difluoro-3-(4-fluorophenyl)-propyl]ester To a stirred solution of 1-(3-bromo-1,1-difluoro-propyl)-4-fluoro-benzene (synthesized according to the methods described in sections a) to e) of example 1) (0.25 g, 1.2 mmol) in dry DMF (1 ml) is added potassium thioacetate (0.41 g, 3.60 mmol) at RT. The reaction mixture is heated at 60° C. for 1.5 h. After completion of the reaction, the mixture is diluted with water (30 ml) and extracted with EtOAc (3×30 ml). The organic layer is washed with water (30 ml), brine (30 ml), dried over anhydrous sodium sulfate and evaporated to get the crude product, which is purified by column chromatography (silica gel, 1% EtOAc/hexane) to yield ethanethioic acid S-[3,3-difluoro-3-(4-fluorophenyl)-propyl]ester (0.26 g, 1.05 mmol, 88%).

b) Synthesis of 3,3-difluoro-3-(4-fluorophenyl)-propane-1-thiol

To a solution of ethanethioic acid S—[3,3-difluoro-3-(4-fluorophenyl)-propyl]ester (0.26 g, 1.05 mmol) in EtOH (3 ml) is added 35% aqueous sodium hydroxide (3 ml) at 0° C. and the reaction mixture is stirred at RT for 1 h. After completion of the reaction, the solvent is distilled off and the residue is diluted with water (10 ml) before acidification with 2N hydrochloric acid to pH 2. The aqueous layer is extracted with EtOAc (3×15 ml) and the combined organic layers are washed with water (20 ml), brine (20 ml), dried over anhydrous sodium sulfate and evaporated to get 3,3-difluoro-3-(4-fluorophenyl)-propane-1-thiol (0.20 g, 0.97 mmol, 92%), which is used in the next step without further purification.

c) Synthesis of 3-fluoro-pyridine-2-carboxylic acid

To a solution of 1,4-diazabicyclo[2.2.2]octane (1.15 g, 10.3 mmol) in diethylether (50 ml) is added n-butyllithium (2.6M in hexane) (3.95 ml, 10.3 mmol) at −78° C. The reaction mixture is stirred at −20° C. for 1 h followed by the addition of a solution of 3-fluoro-pyridine (1.00 g, 10.29 mmol) in diethylether (30 ml) at −78° C. The yellow suspension is stirred at −60° C. for 1 h and then cooled to −78° C. followed by the addition of excess dry ice. The resulting solution allowed to warm to to −10° C. over 20 min. The precipitate is filtered and the residue is washed with ether which yields pure 3-fluoro-pyridine-2-carboxylic acid (1.20 g, 8.51 mmol, 83%).

d) Synthesis of 3-fluoro-N-(3-methyl-butyl)-pyridine-2-carboxylic acid amide To a solution of 3-fluoro-pyridine-2-carboxylic acid (0.50 g, 3.54 mmol) in dimethylformamide (6 ml) are added O-(benzotriazol-1-yl)-N,N,N',N'-tetramethyluronium tetrafluoroborate (3.41 g, 10.63 mmol) and N-methylmorpholine (1.56 ml, 14.2 mmol) at 0° C. followed by the addition of 3-methyl-butyl-amine (0.61 ml, 5.32 mmol). The reaction mixture is stirred at RT for 2 h. After completion of the reaction, the mixture is poured onto ice-water, extracted with EtOAc (3×50 ml). The combined organic layers are washed with brine (50 ml), dried over sodium sulfate and evaporated to dryness to yield the crude product, which is purified by column chromatography (silica gel, 50% EtOAc/hexane) affording 3-fluoro-N-(3-methyl-butyl)-pyridine-2-carboxylic acid amide (0.31 g, 1.47 mmol, 42%).

e) Synthesis of 3-[[3,3-Difluoro-3-(4-fluorophenyl)-propyl]sulfanyl]-N-(3-methyl-butyl)-pyridine-2-carboxylic acid amide To a solution of 3,3-difluoro-3-(4-fluorophenyl)-propane-1-thiol (0.19 g, 0.92 mmol) in DMF (5 ml) in sealed tube are added 3-fluoro-N-(3-methyl-butyl)-pyridine-2-carboxylic acid amide (0.19 g, 0.92 mmol) and cesium carbonate (1.50 g, 4.60 mmol). The reaction mixture is heated at 90° C. for 2 h. After completion of the reaction, the reaction mixture is poured onto ice-water, extracted with EtOAc (3×30 ml). The combined organic layers are washed with brine (50 ml), water (30 ml), dried over sodium sulfate and evaporated to dryness to yield the crude product, which is purified by column chromatography (silica gel, 30% EtOAc/hexane) affording 3-[[3,3-Difluoro-3-(4-fluorophenyl)-propyl]sulfanyl]-N-(3-methyl-butyl)-pyridine-2-carboxylic acid amide (example 3) (0.15 g, 0.37 mmol, 41%). [M+H]$^+$ 397.1.

Synthesis of Example 5

4-[[3,3-Difluoro-3-(4-fluorophenyl)-propyl]sulfanyl]-N-(3-methyl-butyl)-pyridine-3-carboxylic acid amide

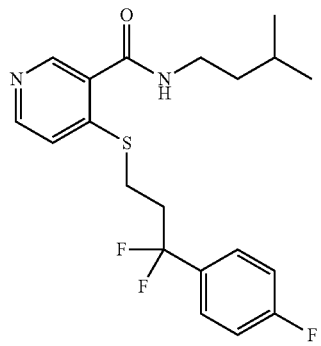 [SMILES: CC(C)CCNC(=O)c1cnccc1SCCC(F)(F)c1ccc(F)cc1]

a) Synthesis of 4-chloro-pyridine-3-carboxylic acid ethyl ester

A suspension of 4-chloro-pyridine-3-carboxylic acid (5.0 g, 31.7 mmol) in thionyl chloride (100 ml) is heated at 80° C. for 1.5 h. The reaction mixture is cooled to RT and excess thionyl chloride is distilled off. The crude product is azeotropped with toluene (3×30 ml) to afford a solid, which is added in portions to a mixture of ethanol (40 ml) and diisopropylethylamine (25 ml) at 0° C. The resulting reaction mixture is stirred at RT for 4 h. After completion of the reaction, the mixture is evaporated to dryness; the residue is diluted with water (20 ml) and extracted with EtOAc (3×25 ml). The combined organic layers are washed with water (30 ml), brine (30 ml), dried over anhydrous sodium sulfate and evaporated to get 4-chloro-pyridine-3-carboxylic acid ethyl ester (4.50 g, 24.3 mmol, 77%), which is used in the next step without further purification.

b) Synthesis of 4-(2-methoxycarbonyl-ethylsulfanyl)-pyridine-3-carboxylic acid ethyl ester To a stirred solution of 4-chloro-pyridine-3-carboxylic acid ethyl ester (4.30 g, 23.2 mmol) in dry tetrahydrofuran (45 ml) is added potassium tert-butoxide (3.12 g, 27.9 mmol) portion wise at 0° C., followed by the addition of methyl 3-mercaptopropanoate (3.35 g, 27.9 mmol). The reaction mixture is stirred at RT for 2 h. After completion of the reaction, the solvent is distilled off and the residue is diluted with water (30 ml). The aqueous layer is extracted with EtOAc (3×40 ml). The combined organic layers are washed with water (40 ml), brine (40 ml), dried over anhydrous sodium sulfate and evaporated to get the crude product, which is purified by column chromatography (silica gel, 30% EtOAc/hexane) to get 4-(2-methoxycarbonyl-ethylsulfanyl)-pyridine-3-carboxylic acid ethyl ester (3.0 g, 11.2 mmol, 48%).

c) Synthesis of 4-mercapto-pyridine-3-carboxylic acid ethyl/methyl ester

Pieces of metallic sodium (0.77 g, 33.5 mmol) are added portion wise to MeOH (70 ml) at 0° C. After complete dissolution of all sodium pieces a solution of 4-(2-methoxycarbonyl-ethylsulfanyl)-pyridine-3-carboxylic acid ethyl ester (3.00 g, 11.1 mmol) in MeOH (10 ml) is added to the solution at RT and the reaction mixture is stirred at 70° C. for 1.5 h. After completion of the reaction, the solvent is distilled off and the residue is diluted with water (30 ml) and washed with EtOAc (40 ml). The washing is rejected. The aqueous layer is acidified with 1M hydrochloric acid and extracted with EtOAc (3×40 ml). The organic layer is washed with water (30 ml), brine (30 ml), dried over anhydrous sodium sulfate and evaporated to get mixture of compounds the corresponding methyl and ethyl esters respectively (1.0 g), which is used in the next step without further purification.

d) Synthesis of 4-[[3,3-difluoro-3-(4-fluorophenyl)-propyl]sulfanyl]-pyridine-3-carboxylic acid ethyl/methyl ester To a stirred solution of 4-mercapto-pyridine-3-carboxylic acid ethyl/methyl ester (1.00 g, ~5.46 mmol) in acetone (30 ml) is added potassium carbonate (1.50 g, 10.9 mmol) at RT followed by the addition of 1-(3-bromo-1,1-difluoro-propyl)-4-fluoro-benzene (synthesized according to the methods described in sections a) to e) of example 1) (1.38 g, 5.46 mmol). The reaction mixture is stirred at 70° C. for 2.5 h. After completion of the reaction, the solvent is distilled off and the residue is diluted with water (30 ml) before extraction with EtOAc (3×30 ml). The combined organic layers are washed with water (50 ml), brine (50 ml), dried over anhydrous sodium sulfate and evaporated to get mixture of ethyl and methyl esters of 4-[[3,3-Difluoro-3-(4-fluorophenyl)-propyl]sulfanyl]-pyridine-3-carboxylic acid respectively, which is purified by column chromatography (silica gel, 15% EtOAc/hexane) affording 0.6 g material.

e) Synthesis of 4-[[3,3-difluoro-3-(4-fluorophenyl)-propyl]sulfanyl]-pyridine-3-carboxylic acid To a stirred solution of compound 4-[[3,3-difluoro-3-(4-fluorophenyl)-propyl]sulfanyl]-pyridine-3-carboxylic acid ethyl/methyl ester (0.60 g, ~1.69 mmol) in EtOH (20 ml) is added a solution of sodium hydroxide (0.13 g, 3.38 mmol) in water (20 ml) at RT. The reaction mixture is stirred at RT for 2 h. After completion of the reaction, the solvent is distilled off; the residue is diluted with water (15 ml) and washed with EtOAc (20 ml). The aqueous layer is acidified with 1M hydrochloric acid to pH 4 and extracted with EtOAc (3×30 ml). The combined organic layers is washed with water (30 ml), brine (30 ml), dried over anhydrous sodium sulfate and evaporated to get 4-[[3,3-difluoro-3-(4-fluorophenyl)-propyl]sulfanyl]-pyridine-3-carboxylic acid (0.40 g, 1.22 mmol, 11%, 3 steps), which is used in the next step without further purification.

f) Synthesis of 4-[[3,3-difluoro-3-(4-fluorophenyl)-propyl]sulfanyl]-N-(3-methyl-butyl)-pyridine-3-carboxylic acid amide To a stirred solution of 4-[[3,3-difluoro-3-(4-fluorophenyl)-propyl]sulfanyl]-pyridine-3-carboxylic acid (0.15 g, 0.46 mmol) in dry tetrahydrofuran (6 ml) are added O-(7-azabenzotriazol-1-yl)-N,N,N',N'-tetramethyluronium hexafluorophosphate (0.35 g, 0.91 mmol) and diisopropylethylamine (0.32 ml, 1.82 mmol) at RT. The reaction mixture is stirred for 5 min at RT followed by the addition of 3-methyl-butyl-amine (0.06 ml, 0.50 mmol). The reaction mixture is stirred at RT for 2 h. After completion of the reaction, the solvent is distilled off and the residue is diluted with saturated sodium hydrogen carbonate solution (20 ml) before extraction with EtOAc (3×30 ml). The organic layer is washed with saturated ammonium chloride solution (30 ml), water (30 ml), brine (30 ml), dried over anhydrous sodium sulfate and evaporated in vacuo to get the crude product, which is purified by column chromatography (silica gel, 15% acetone/hexane) to yield of 4-[[3,3-difluoro-3-(4-fluorophenyl)-propyl]sulfanyl]-N-(3-methyl-butyl)-pyridine-3-carboxylic acid amide (example 5) (0.13 g, 0.33 mmol, 71%). [M+H]+ 397.1.

Synthesis of Example 7

3-[[3,3-Difluoro-3-(4-fluorophenyl)-propyl]sulfanyl]-N-(3-methyl-butyl)-pyridine-4-carboxylic acid amide

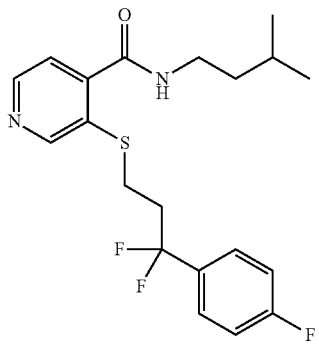 [SMILES: CC(C)CCNC(=O)c1ccncc1SCCC(F)(F)c1ccc(F)cc1]

a) Synthesis of 3-[[3,3-difluoro-3-(4-fluorophenyl)-propyl]sulfanyl]-pyridine-4-carboxylic acid methyl ester To a solution of 3-chloro-pyridine-4-carboxylic acid methyl ester (0.28 g, 1.65 mmol) in DMF (10 ml) are added cesium carbonate (2.68 g, 8.25 mmol) and 3,3-difluoro-3-(4-fluorophenyl)-propane-1-thiol (synthesized according to the methods described in sections a) and b) of example 3) (0.34 g, 1.65 mmol) in a sealed tube. The reaction mixture is stirred at 90° C. for 1 h. After completion of the reaction, the mixture is diluted with water (15 ml) and extracted with EtOAc (3×20 ml). The organic layer is washed with water (20 ml), brine (20 ml), dried over anhydrous sodium sulfate and evaporated to get the crude product, which is purified by column chromatography (silica gel, 10% acetone/hexane) to yield 3-[[3,3-difluoro-3-(4-fluorophenyl)-propyl]sulfanyl]-pyridine-4-carboxylic acid methyl ester (0.19 g, 0.56 mmol, 34%).

b) Synthesis of 3-[[3,3-difluoro-3-(4-fluorophenyl)-propyl]sulfanyl]-pyridine-4-carboxylic acid To a solution of 3-[[3,3-difluoro-3-(4-fluorophenyl)-propyl]sulfanyl]-pyridine-4-carboxylic acid methyl ester (0.33 g, 0.96 mmol) in EtOH (10 ml) are added sodium hydroxide (0.15 g, 3.87 mmol) and water (10 ml). The reaction mixture is stirred at 80° C. for 1 h. After completion of the reaction, the solvent is evaporated and the residue is diluted with water (10 ml). The aqueous layer is acidified with 2M hydrochloric acid to pH 3 and extracted with EtOAc (3×20 ml). The combined organic layers are washed with water (20 ml), brine (20 ml), dried over anhydrous sodium sulfate and evaporated to get the crude 3-[[3,3-difluoro-3-(4-fluorophenyl)-propyl]sulfanyl]-pyridine-4-carboxylic acid (0.26 g, 0.8 mmol, 82%), which is used in the next step without further purification.

c) Synthesis of 3-[[3,3-difluoro-3-(4-fluorophenyl)-propyl]sulfanyl]-N-(3-methyl-butyl)-pyridine-4-carboxylic acid amide To a stirred solution of 3-[[3,3-difluoro-3-(4-fluorophenyl)-propyl]sulfanyl]-pyridine-4-carboxylic acid (0.26 g, 0.79 mmol) in DCM (10 ml) are added O-(7-azabenzotriazol-1-yl)-N,N,N',N'-tetramethyluronium hexafluorophosphate (0.60 g, 1.60 mmol) and diisopropylethylamine (0.55 ml, 3.18 mmol) at 0° C. The reaction mixture is stirred for 5 min at 0° C. followed by the addition of 3-methyl-butyl-amine (0.11 ml, 0.95 mmol). The reaction mixture is stirred at RT for 3 h. After completion of the reaction, the solvent is distilled off and the residue is diluted with saturated sodium hydrogen carbonate solution (20 ml) before extraction with EtOAc (3×30 ml). The organic layer is washed with saturated ammonium chloride solution (30 ml), water (30 ml), brine (30 ml), dried over anhydrous sodium sulfate and evaporated in vacuo to get the crude product, which is purified by column chromatography (silica gel, 20% acetone/hexane) to yield of 3-[[3,3-difluoro-3-(4-fluorophenyl)-propyl]sulfanyl]-N-(3-methyl-butyl)-pyridine-4-carboxylic acid amide (example 7) (0.22 g, 0.55 mmol, 70%). [M+H]+ 397.1.

Synthesis of Example 14

4-[[3,3-Difluoro-3-(4-fluorophenyl)-propyl]sulfanyl]-N-[(4-fluorophenyl)-methyl]-thiazole-5-carboxylic acid amide

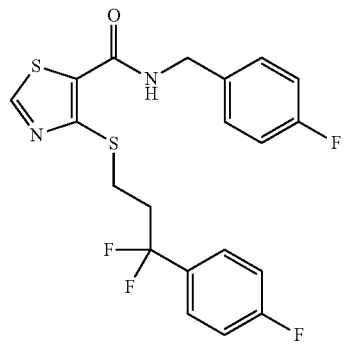 [SMILES: O=C(NCc1ccc(F)cc1)c1scnc1SCCC(F)(F)c1ccc(F)cc1]

a) Synthesis of 4-(2-methoxycarbonyl-ethylsulfanyl)-thiazole-5-carboxylic acid methyl ester A solution of 2-isocyano-acetic acid ethyl ester (10.0 g, 88.4 mmol) in tetrahydrofuran (80 ml) is added to a suspension of potassium tert-butoxide (10.9 g, 97.2 mmol) in tetrahydrofuran (70 ml) at −40° C. The mixture is cooled to −60° C. followed by drop wise addition of carbon disulfide (5.3 ml). The mixture is warmed to 10° C. and methyl 3-bromopropionic acid methyl ester (9.7 ml, 88.4 mmol) is added. The resulting mixture is allowed to warm to RT, stirred for 2 h and then concentrated. 4-(2-Methoxycarbonyl-ethylsulfanyl)-thiazole-5-carboxylic acid methyl ester is obtained by crystallization of the crude mixture from DCM/hexane (15.2 g, 58.2 mmol, 66%).

b) Synthesis of 4-mercapto-thiazole-5-carboxylic acid methyl ester

Sodium hydroxide (0.29 g, 7.27 mmol) is added to a solution of 4-(2-methoxycarbonyl-ethylsulfanyl)-thiazole-5-carboxylic acid methyl ester (2.0 g, 7.27 mmol) in MeOH (30 ml). The mixture is refluxed at 70-80° C. for 1 h and then concentrated in vacuo. The residue is dissolved in EtOAc/water (1:1) (80 ml) and the pH is adjusted to 2 with 2M hydrochloric acid. The organic layer is dried over sodium sulfate and concentrated yielding 4-mercapto-thiazole-5-carboxylic acid methyl ester (0.82 g, 4.67 mmol, 46%).

c) Synthesis of 4-[[3,3-difluoro-3-(4-fluorophenyl)-propyl]sulfanyl]-thiazole-5-carboxylic acid methyl ester 4-Mercapto-thiazole-5-carboxylic acid methyl ester (0.41 g, 2.16 mmol) is dissolved in DMF (6 ml) and triethylamine (0.45 ml, 3.24 mmol) and 1-(3-bromo-1,1-difluoro-propyl)-4-fluoro-benzene (synthesized according to the methods described in sections a) to e) of example 1) (0.55 g, 2.16 mmol) are added successively. The resulting mixture is stirred at RT for 16 h. After completion of the reaction, the mixture is poured onto water (20 ml) and extracted with EtOAc (3×30 ml). The combined organic layers are washed with brine (20 ml), dried over sodium sulfate and concentrated to dryness. The crude is purified by column chromatography (silica gel, 20% EtOAc/hexane) yielding 4-[[3,3-difluoro-3-(4-fluorophenyl)-propyl]sulfanyl]-thiazole-5-carboxylic acid methyl ester (0.42 g, 1.2 mmol, 56%).

d) Synthesis of 4-[[3,3-difluoro-3-(4-fluorophenyl)-propyl]sulfanyl]-thiazole-5-carboxylic acid 4-[[3,3-Difluoro-3-(4-fluorophenyl)-propyl]sulfanyl]-thiazole-5-carboxylic acid methyl ester (0.88 g, 2.54 mmol) is taken in EtOH/water (1:1) (4 ml) powdered KOH (0.36 g, 6.34 mmol) is added. The mixture is refluxed vigorously at 120° C. for 16 h. After completion of the reaction, EtOH is evaporated. The residue is diluted with water (20 ml), acidified with 2M hydrochloric acid to pH 3, and extracted with EtOAc (3×30 ml). The combined organic layers are dried over sodium sulfate, evaporated to dryness yielding 4-[[3,3-difluoro-3-(4-fluorophenyl)-propyl]sulfanyl]-thiazole-5-carboxylic acid (0.7 g, 2.09 mmol, 83%).

e) Synthesis of 4-[[3,3-difluoro-3-(4-fluorophenyl)-propyl]sulfanyl]-N-[(4-fluorophenyl)-methyl]-thiazole-5-carboxylic acid amide To a solution of 4-[[3,3-difluoro-3-(4-fluorophenyl)-propyl]sulfanyl]-thiazole-5-carboxylic acid (0.15 g, 0.45 mmol) in DMF (3 ml) are added O-(benzotriazol-1-yl)-N,N,N',N'-tetramethyluronium tetrafluoroborate (216 mg, 0.68 mmol) and N-methylmorpholine (0.01 ml, 0.9 mmol) at 0° C. followed by the addition of 4-fluorobenzyl amine (67 mg, 0.54 mmol). The reaction mixture is stirred at RT for 3 h. After completion of the reaction, the mixture is poured onto ice-water, extracted with EtOAc (3×50 ml). The combined organic layers are washed with brine (50 ml), dried over sodium sulfate and evaporated to dryness to yield the crude product, which is purified by column chromatography (silica gel, 15% acetone/hexane) affording 4-[[3,3-difluoro-3-(4-fluorophenyl)-propyl]sulfanyl]-N-[(4-fluorophenyl)-methyl]-thiazole-5-carboxylic acid amide (example 14) (93 mg, 0.21 mmol, 47%). [M+H]+ 441.1.

Synthesis of Example 15

4-[[3,3-Difluoro-3-(4-fluorophenyl)-propyl]sulfanyl]-N-[(4-fluorophenyl)-methyl]-2-methyl-thiazole-5-carboxylic acid amide

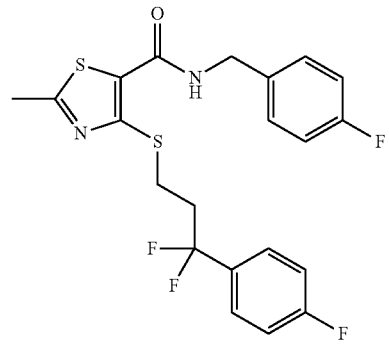 [SMILES: Cc1nc(SCCC(F)(F)c2ccc(F)cc2)c(C(=O)NCc2ccc(F)cc2)s1]

a) Synthesis of 4-hydroxy-2-methyl-thiazole-5-carboxylic acid ethyl ester

A mixture of ethyl 2-bromo-propanedioic acid diethyl ester (32.0 g, 133.2 mmol) and thioacetamide (10.0 g, 133.2 mmol) in toluene (130 ml) is refluxed for 4 h and then cooled. The insoluble material is filtered off and the filtrate is concentrated. The residue is suspended in diisopropyl ether and collected by filtration to give the 4-hydroxy-2-methyl-thiazole-5-carboxylic acid ethyl ester (7.2 g, 38.5 mmol, 29%).

b) Synthesis of 4-(dimethyl-carbamothioyl)oxy-2-methyl-thiazole-5-carboxylic acid ethyl ester To a mixture of 4-hydroxy-2-methyl-thiazole-5-carboxylic acid ethyl ester (7.2 g, 37.4 mmol) and 1,8-diazabicyclo [5.4.0]undec-7-ene (11.2 ml, 74.8 mmol) in DMF (50 ml) is added N,N-dimethyl-carbamothioyl chloride (6.94 g, 56.1 mmol). The mixture is stirred at RT for 14 h and at 60° C. for 3 h, poured onto water (100 ml) and extracted with EtOAc (3×50 ml). The combined organic layers are washed with water (2×50 ml), dried over sodium sulfate and concentrated. The residue is chromatographed (silica gel, 10% EtOAc/hexane) to give 4-(dimethyl-carbamothioyl)oxy-2-methyl-thiazole-5-carboxylic acid ethyl ester (5.7 g, 20.7 mmol, 55%).

c) Synthesis of 4-[(dimethyl-carbamoyl)sulfanyl]-2-methyl-thiazole-5-carboxylic acid ethyl ester A mixture of 4-(dimethyl-carbamothioyl)oxy-2-methyl-thiazole-5-carboxylic acid ethyl ester (1.8 g, 6.57 mmol) and diphenyl ether (12 mL) is heated at 190° C. for 6 h, cooled, and chromatographed (silica gel, 45% EtOAc/hexane) to afford 4-[(dimethyl-carbamoyl)sulfanyl]-2-methyl-thiazole-5-carboxylic acid ethyl ester (0.85 g, 3.08 mmol, 47%).

d) Synthesis of 4-mercapto-2-methyl-thiazole-5-carboxylic acid ethyl ester

To a mixture of 4-[(dimethyl-carbamoyl)sulfanyl]-2-methyl-thiazole-5-carboxylic acid ethyl ester (0.84 g, 3.06 mmol) in MeOH (30 ml) is added sodium hydride (60% oil dispersion) (0.4 g, 10.1 mmol). The mixture is refluxed for 1 h under an atmosphere of nitrogen and concentrated. The residue is treated with 1M hydrochloric acid and extracted with EtOAc (3×30 ml). The combined organic layers are washed with brine (30 ml), dried over sodium sulfate and concentrated to give 4-mercapto-2-methyl-thiazole-5-carboxylic acid ethyl ester (0.58 g, 2.83 mmol, 94%), which is used in the next step without further purification.

e) Synthesis of 4-[[3,3-difluoro-3-(4-fluorophenyl)-propyl]sulfanyl]-2-methyl-thiazole-5-carboxylic acid ethyl ester To a solution of give 4-mercapto-2-methyl-thiazole-5-carboxylic acid ethyl ester (0.58 g, 2.83 mmol) in acetone (10 ml) are added 1-(3-bromo-1,1-difluoro-propyl)-4-fluoro-benzene (synthesized according to the methods described in sections a) to e) of example 1) (0.72 g, 2.83 mmol) and potassium carbonate (0.78 g, 5.66 mmol) an the mixture is heated at 80° C. for 16 h. Acetone is evaporated, diluted with water (40 ml) and extracted with EtOAc (3×30 ml). The crude product is purified by column chromatography (silica gel, 10% EtOAc/hexane) yielding 4-[[3,3-difluoro-3-(4-fluorophenyl)-propyl]sulfanyl]-2-methyl-thiazole-5-carboxylic acid ethyl ester (0.6 g, 1.6 mmol, 56%).

f) Synthesis of 4-[[3,3-difluoro-3-(4-fluorophenyl)-propyl]sulfanyl]-2-methyl-thiazole-5-carboxylic acid To a solution of 4-[[3,3-difluoro-3-(4-fluorophenyl)-propyl]sulfanyl]-2-methyl-thiazole-5-carboxylic acid ethyl ester (0.6 g, 1.6 mmol) in EtOH (1.5 ml) is added an aqueous solution (1.5 ml) of potassium carbonate (0.22 g, 4.0 mmol) and the mixture is stirred at RT for 16 h. After completion of the reaction, the solvent is evaporated and the residue is diluted with water (30 ml), acidified with 2M hydrochloric acid to pH 3 and extracted with EtOAc (3×40 ml) yielding 4-[[3,3-difluoro-3-(4-fluorophenyl)-propyl]sulfanyl]-2-methyl-thiazole-5-carboxylic acid (0.41 g, 1.19 mmol, 74%).

g) Synthesis of 4-[[3,3-difluoro-3-(4-fluorophenyl)-propyl]sulfanyl]-N-[(4-fluorophenyl)-methyl]-2-methyl-thiazole-5-carboxylic acid amide To a solution of 4-[[3,3-difluoro-3-(4-fluorophenyl)-propyl]sulfanyl]-2-methyl-thiazole-5-carboxylic acid (0.25 g, 0.72 mmol) in DMF (4 ml) are added O-(benzotriazol-1-yl)-N,N,N',N'-tetramethyluronium tetrafluoroborate (347 mg, 1.08 mmol) and N-methylmorpholine (0.16 ml, 1.44 mmol) at 0° C. followed by the addition of 4-fluorobenzyl amine (0.01 ml, 0.86 mmol). The reaction mixture is stirred at RT for 3 h. After completion of the reaction, the mixture is poured onto ice-water, extracted with EtOAc (3×15 ml). The combined organic layers are washed with brine (20 ml), dried over sodium sulfate and evaporated to dryness to yield the crude product, which is purified by column chromatography (silica gel, 5% acetone/hexane) followed by preparative HPLC affording 4-[[3,3-difluoro-3-(4-fluorophenyl)-propyl]sulfanyl]-N-[(4-fluorophenyl)-methyl]-2-methyl-thiazole-5-carboxylic acid amide (example 15) (0.2 g, 0.42 mmol, 36%). [M+H]+ 455.1.

Synthesis of Further Examples

The synthesis of further examples was carried out according to the methods already described. Table 1 shows which compound were produced according to which method. It is evident to the person skilled in the art which educts and reagents were used in each case.

TABLE 1

| Example | Chemical name | Preparation according to example | MS m/z [M + H]+ |
|---|---|---|---|
| 2 | N-(3,3-Dimethyl-butyl)-2-[3-(4-fluorophenyl)-propylsulfanyl]-benzamide | 1 | 374.1 |
| 4 | 3-[2-(Benzenesulfonyl)-ethylsulfanyl]-N-(thiophen-2-yl-methyl)-pyridine-2-carboxylic acid amide | 1 | 419.1 |
| 6 | 4-[[3,3-Difluoro-3-(4-fluorophenyl)-propyl]sulfanyl]-N-[(4-fluorophenyl)-methyl]-pyridine-3-carboxylic acid amide | 5 | 435.0 |
| 8 | 3-[2-(Benzenesulfonyl)-ethylsulfanyl]-N-(thiophen-2-yl-methyl)-pyridine-4-carboxylic acid amide | 1 | 419.1 |
| 9 | 3-[[3,3-Difluoro-3-(4-fluorophenyl)-propyl]sulfanyl]-N-(3-methyl-butyl)-pyrazine-2-carboxylic acid amide | 1 | 398.1 |
| 10 | 4-[[3,3-Difluoro-3-(4-fluorophenyl)-propyl]sulfanyl]-N-(3-methyl-butyl)-pyrimidine-5-carboxylic acid amide | 5 | 398.1 |
| 11 | 4-[[3,3-Difluoro-3-(4-fluorophenyl)-propyl]sulfanyl]-N-[(4-fluorophenyl)-methyl]-pyrimidine-5-carboxylic acid amide | 5 | 436.0 |
| 12 | 3-[[3,3-Difluoro-3-(4-fluorophenyl)-propyl]sulfanyl]-N-(3-methyl-butyl)-pyridazine-4-carboxylic acid amide | 7 | 398.1 |
| 13 | 3-[[3,3-Difluoro-3-(4-fluorophenyl)-propyl]sulfanyl]-N-[(4-fluorophenyl)-methyl]-pyridazine-4-carboxylic acid amide | 7 | 436.0 |

Pharmacological Experiments

Fluorescence Assay Using a Voltage Sensitive Dye (Fluorimetry)

Human CHO-K1 cells expressing KCNQ2/3 channels are cultivated adherently at 37° C., 5% $CO_2$ and 95% humidity in cell culture bottles (e.g. 80 cm² TC flasks, Nunc) with DMEM-high glucose (Sigma Aldrich, D7777) including 10% FCS (PAN Biotech, e.g. 3302-P270521) or alternatively MEM Alpha Medium (1×, liquid, Invitrogen, #22571), 10% fetal calf serum (FCS) (Invitrogen, #10270-106, heat-inactivated) and the necessary selection antibiotics.

Before being sown out for the measurements, the cells are washed with 1×DPBS buffer $Ca^{2+}/Mg^{2+}$-free (e.g. Invitrogen, #14190-094) and detached from the bottom of the culture vessel by using Accutase (PAA Laboratories, #L11-007) (incubation with Accutase for 15 min at 37° C.). The cell number is determined using a CASY™ cell counter (TCC, Schärfe System). Depending on the optimal density for each individual cell line, 20,000-30,000 cells/well/100 µl are seeded onto 96-well Corning™ CellBIND™ assay plates (Flat Clear Bottom Black Polystyrene Microplates, #3340). Freshly seeded cells are then left to settle for one hour at room temperature, followed by incubation for 24 hours at 37° C., 5% $CO_2$ and 95% humidity.

The voltage-sensitive fluorescent dye from the Membrane Potential Assay Kit (Red™ Bulk format part R8123 for FLIPR, MDS Analytical Technologies™) is prepared by dissolving the contents of one vessel *Membrane Potential Assay Kit Red Component A* in 200 ml of extracellular buffer (ES buffer, 120 mM NaCl, 1 mM KCl, 10 mM HEPES, 2 mM $CaCl_2$, 2 mM $MgCl_2$, 10 mM glucose; pH 7.4). After removal of the nutrient medium, the cells are washed once with 200 µl of ES buffer, then loaded for 45 min at room temperature in 100 µl of dye solution in the dark.

Fluorescence measurements are carried out in a BMG Labtech FLUOstar™, BMG Labtech NOVOstar™ or BMG Labtech POLARstar™ instrument (525 nm excitation, 560 nm emission, Bottom Read mode). After incubation with the dye, 50 µl of the test substances in the desired concentrations, or 50 µl of ES buffer for control purposes, are applied to the wells of the assay plate and incubated for 30 min at room temperature while being shielded from light. The fluorescence intensity of the dye is then measured for 5 min and the fluorescence value $F_1$ of each well is thus determined at a given, constant time. 15 µl of a KCl solution are then added to each well (final concentration of potassium ions 92 mM). The change in fluorescence intensity is subsequently monitored until all the relevant values have been obtained (mainly 5-30 min). At a given time post KCl application, a fluorescence value $F_2$ is determined, in this case at the time of the fluorescence peak.

For calculation, the fluorescence intensity $F_2$ is corrected for the fluorescence intensity $F_1$, and the activity (ΔF/F) of the target compound on the potassium channel is determined as follows:

$$\left(\frac{F_2 - F_1}{F_1}\right) \times 100 = \frac{\Delta F}{F}(\%)$$

In order to determine whether a substance has agonistic activity, $$\left(\frac{\Delta F}{F}\right)_K$$

can be related to $$\frac{\Delta F}{F}$$

of control wells.

$$\left(\frac{\Delta F}{F}\right)_K$$

is determined by adding to the well only the buffer solution instead of the test substance, determining the value $F_{1K}$ of the fluorescence intensity, adding the potassium ions as described above, and measuring a value $F_{2K}$ of the fluorescence intensity. $F_{2K}$ and $F_{1K}$ are then calculated as follows:

$$\left(\frac{F_{2K} - F_{1K}}{F_{1K}}\right) \times 100 = \left(\frac{\Delta F}{F}\right)_K (\%)$$

A substance has an agonistic activity on the potassium channel if $$\frac{\Delta F}{F}$$

is greater than $$\left(\frac{\Delta F}{F}\right)_K : \frac{\Delta F}{F} > \left(\frac{\Delta F}{F}\right)_K$$

Independently of the comparison of $$\frac{\Delta F}{F}$$

with $$\left(\frac{\Delta F}{F}\right)_K$$

it is possible to conclude that a target compound has agonistic activity if $$\frac{\Delta F}{F}$$

increases dose dependently.

Calculations of $EC_{50}$ and $IC_{50}$ values are carried out with the aid of 'Prism v4.0' software (GraphPad Software™).

Pharmacological Data

The pharmacological effects of the compounds according to the invention were determined as described hereinbefore (pharmacological experiments).

The corresponding pharmacological data are summarized in Table 2.

TABLE 2

| Example | Fluorimetry % Efficacy (retigabine = 100%) | Fluorimetry $EC_{50}/IC_{50}$ [nM] |
|---|---|---|
| 1 | 203 | 156 |
| 2 | 186 | 501 |
| 3 | 118 | 1588 |
| 5 | 228 | 849 |
| 6 | 121 | 563 |
| 7 | 197 | 1399 |
| 9 | 199 | 521 |
| 10 | 211 | 61 |
| 11 | 112 | 51 |
| 12 | 203 | 427 |
| 13 | 100 | 264 |
| 15 | 83 | 231 |

The invention claimed is:

1. A compound of general formula (I)

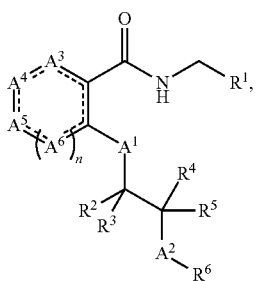

wherein $A^1$ represents $CR^{10}R^{11}$ or S;

$A^2$ represents $CR^{12}R^{13}$, $C(=O)$, O, S, $S(=O)$ or $S(=O)_2$;

$A^3$, $A^4$ and $A^5$ independently of each other represent $CR^7$, N, O, S or $NR^8$, $A^6$ represents $CR^7$ or N, and n denotes 0 or 1, with the proviso, that if n denotes 0, then precisely one of $A^3$, $A^4$ and $A^5$ represents O, S or $NR^8$, or if n denotes 1, then $A^3$, $A^4$ and $A^5$ independently of each other represent $CR^7$ or N;

and with the proviso, that if n denotes 1 and $A^3$, $A^4$ and $A^5$ each represent $CR^7$, then $A^6$ does not represent N;

$R^1$ represents $C_{1-10}$-aliphatic residue, unsubstituted or mono- or polysubstituted;

$C_{3-10}$-cycloaliphatic residue or a 3 to 10 membered heterocycloaliphatic residue, in each case unsubstituted or mono- or polysubstituted and in each case optionally linked via a $C_{1-4}$-aliphatic group, which in turn is optionally unsubstituted or mono- or polysubstituted;

aryl or heteroaryl, in each case unsubstituted or mono- or polysubstituted and in each case optionally linked via a $C_{1-4}$-aliphatic group, which in turn is optionally unsubstituted or mono- or polysubstituted;

$R^2$, $R^3$, $R^4$, $R^5$, $R^{10}$, $R^{11}$, $R^{12}$ and $R^{13}$ each independently of another represent H; F; Cl; Br; I; $NO_2$; $CF_3$; CN; OH; $OCF_3$; SH; $SCF_3$; $C_{1-10}$-aliphatic residue, O—$C_{1-10}$-aliphatic residue or S—$C_{1-10}$-aliphatic residue, in each case saturated or unsaturated, branched or unbranched, unsubstituted or mono- or poly-substituted;

or $C_{3-10}$-cycloaliphatic residue, saturated or unsaturated, branched or unbranched, unsubstituted or mono- or poly-substituted;

or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{11}$ and $R^{13}$, together with the carbon atom(s) joining them, form a $C_{3-10}$-cycloaliphatic residue or a 3 to 10 membered heterocycloaliphatic residue, in each case saturated or unsaturated, unsubstituted or mono- or poly-substituted; wherein the remaining substituents $R^2$, $R^3$, $R^4$, $R^5$, $R^{10}$, $R^{11}$, $R^{12}$ and $R^{13}$ in each case have the meaning given above;

$R^6$ represents a $C_{3-10}$-cycloaliphatic residue or a 3 to 10 membered heterocycloaliphatic residue, in each case saturated or unsaturated, unsubstituted or mono- or poly-substituted;

or represents an aryl or a heteroaryl, in each case unsubstituted or mono- or poly-substituted;

each $R^7$ independently of each other represents H, F; Cl; CN; $CF_3$; $CHF_2$; $CH_2F$; $OCF_3$; $OCHF_2$; $OCH_2F$; $SCF_3$; O—$C_{1-4}$-aliphatic residue, $C_{1-4}$-aliphatic residue or $S(=O)_2$—$C_{1-4}$-aliphatic residue, wherein the $C_{1-4}$-aliphatic residue in each case is optionally saturated or unsaturated, branched or unbranched, unsubstituted or mono- or poly-substituted;

and $R^8$ represents H or a $C_{1-4}$-aliphatic residue, wherein the aliphatic residue is optionally saturated or unsaturated, branched or unbranched, unsubstituted or mono- or poly-substituted;

in which an "aliphatic group" and "aliphatic residue" in each case is optionally branched or unbranched, saturated or unsaturated, in which a "cycloaliphatic residue" and a "heterocycloaliphatic residue" in each case is optionally saturated or unsaturated, in which "mono- or polysubstituted" with respect to an "aliphatic group", an "aliphatic residue", a "cycloaliphatic residue" and a "heterocycloaliphatic residue" relates, with respect to the corresponding residues or groups, to the substitution of one or more hydrogen atoms each independently of one another by at least one substituent selected from the group consisting of F, Cl, Br, I, $NO_2$, $NH_2$, $NH(C_{1-4}$-aliphatic residue), $N(C_{1-4}$-aliphatic residue$)_2$, NH—$C(=O)$—$C_{1-4}$ aliphatic residue, $N(C_{1-4}$-aliphatic residue)-$C(=O)$—$C_{1-4}$-aliphatic residue, NH—$S(=O)_2$—$C_{1-4}$-aliphatic residue, $N(C_{1-4}$-aliphatic residue)-$S(=O)_2$—$C_{1-4}$-aliphatic residue, OH, $OCF_3$, O—$C_{1-4}$-aliphatic residue, O—$C(=O)$—$C_{1-4}$-aliphatic residue, SH, $SCF_3$, S—$C_{1-4}$-aliphatic residue, $S(=O)_2OH$, $S(=O)_2$—$C_{1-4}$-aliphatic residue, $S(=O)_2$—O—$C_{1-4}$-aliphatic residue, $S(=O)_2$—$NH(C_{1-4}$-aliphatic residue), $S(=O)_2$—N$(C_{1-4}$-aliphatic residue$)_2$, CN, $CF_3$, CHO, COOH, $C_{1-4}$-aliphatic residue, $C(=O)$—$C_{1-4}$-aliphatic residue, $C(=O)$—O—$C_{1-4}$-aliphatic residue, $C_{3-6}$-cycloaliphatic residue, 3 to 7 membered heterocycloaliphatic residue, benzyl, aryl, heteroaryl, $C(=O)NH_2$, a $C(=O)$—$NH(C_{1-4}$-aliphatic residue) and $C(=O)$—$N(C_{1-4}$-aliphatic residue$)_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

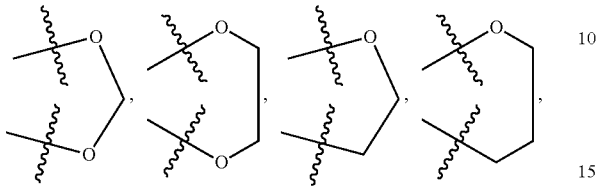

$NH(C_{1-4}$-aliphatic residue), $N(C_{1-4}$-aliphatic residue$)_2$, $NH$—$C(=O)$—$C_{1-4}$-aliphatic residue, $N(C_{1-4}$ aliphatic residue)-$C(=O)$—$C_{1-4}$ aliphatic residue, $NH$—$S(=O)_2$—$C_{1-4}$ aliphatic residue, $N(C_{1-4}$ aliphatic residue)-$S(=O)_2$—$C_{1-4}$ aliphatic residue, OH, $OCF_3$, O—$C_{1-4}$-aliphatic residue, O—$C(=O)$—$C_{1-4}$-aliphatic residue, SH, $SCF_3$, S—$C_{1-4}$-aliphatic residue, $S(=O)_2OH$, $S(=O)_2$—$C_{1-4}$-aliphatic residue, $S(=O)_2$—O—$C_{1-4}$-aliphatic residue, $S(=O)_2$—NH($C_{1-4}$-aliphatic residue), $S(=O)_2$—N($C_{1-4}$-aliphatic residue$)_2$, CN, $CF_3$, $C(=O)H$, $C(=O)OH$, $C_{1-4}$-aliphatic residue, $C(=O)$—$C_{1-4}$-aliphatic residue, $C(=O)$—O—$C_{1-4}$-aliphatic residue, $C_{3-6}$-cycloaliphatic residue, 3 to 7 membered heterocycloaliphatic residue, benzyl, aryl, and heteroaryl;
in the form of an individual single stereoisomer or a mixture of the stereoisomers in any mixing ratio, and/or in the form of a free compound, a solvate and and/or a physiologically acceptable salt.

2. The compound according to claim 1, wherein
$A^1$ represents $CR^{10}R^{11}$ or S;
$A^2$ represents $CR^{12}R^{13}$, $C(=O)$, O, S, $S(=O)$ or $S(=O)_2$;
$A^3$, $A^4$ and $A^5$ independently of each other represent $CR^7$, N, O, S or $NR^8$,
$A^6$ represents $CR^7$ or N, and
n denotes 0 or 1,
with the proviso, that
if n denotes 0, then precisely one of $A^3$, $A^4$ and $A^5$ represents O, S or $NR^8$, or
if n denotes 1, then $A^3$, $A^4$ and $A^5$ independently of each other represent $CR^7$ or N;
and with the proviso, that if n denotes 1 and $A^3$, $A^4$ and $A^5$ each represent $CR^7$, then $A^6$ does not represent N;
$R^1$ denotes a $C_{1-10}$-aliphatic residue, unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and $C(=O)OH$,
wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, $C(=O)OH$, $C_{3-6}$-cycloaliphatic residue and a 3 to 7 membered heterocycloaliphatic residue,
wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and O—$C_{1-4}$-aliphatic residue, and
wherein the $C_{3-6}$-cycloaliphatic residue and the 3 to 7 membered heterocycloaliphatic residue is in each case optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and $C(=O)OH$,
and wherein the $C_{3-10}$-cycloaliphatic residue or the 3 to 10 membered heterocycloaliphatic residue is in each case optionally linked via a $C_{1-4}$-aliphatic group, which in turn is optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and $C(=O)OH$,
or denotes an aryl or heteroaryl, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, $C(=O)OH$, $C(=O)CH_3$, $C(=O)C_2H_5$, $C(=O)OCH_3$, $C(=O)OC_2H_5$, $C_{3-6}$ cycloaliphatic residue, 3 to 7 membered heterocycloaliphatic residue,

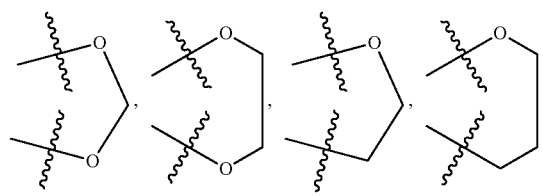

benzyl, phenyl, thienyl, pyridyl, furyl, thiazolyl and oxazolyl,
wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and O—$C_{1-4}$-aliphatic residue, and
wherein benzyl, phenyl, thienyl, pyridyl, furyl, thiazolyl and oxazolyl is in each case optionally unsubstituted or mono- or polysubstituted with at least one substituent selected from the group consisting of F, Cl, Br, $NO_2$, $NH_2$, $NH(C_{1-4}$-aliphatic residue), $N(C_{1-4}$-aliphatic residue$)_2$, OH, O—$C_{1-4}$-aliphatic residue, $OCF_3$, $OCH_2CH_2OH$, $OCH_2OCH_3$, SH, $SCF_3$, S—$C_{1-4}$-aliphatic residue, $CF_3$, CN, $C_{1-4}$-aliphatic residue, $C(=O)OH$, $C(=O)CH_3$, $C(=O)C_2H_5$, $C(=O)OCH_3$, $C(=O)OC_2H_5$, and
wherein the $C_{3-6}$-cycloaliphatic residue and the 3 to 7 membered heterocycloaliphatic residue is in each case optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the aryl or the heteroaryl residue is in each case optionally linked via a $C_{1-4}$-aliphatic group, which in turn is optionally unsubstituted or mono- or polysubstituted with at least one substituent selected from the group consisting of F, Cl, Br, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN and C(=O)OH, $R^2$, $R^3$, $R^4$, $R^5$, $R^{10}$, $R^{11}$, $R^{12}$ and $R^{13}$ each independently of the others represents H; F; Cl; Br; I; $NO_2$; $CF_3$; CN; OH; $OCF_3$; SH; $SCF_3$; $C_{1-4}$-aliphatic residue, O—$C_{1-4}$-aliphatic residue or S—$C_{1-4}$-aliphatic residue, in each case saturated or unsaturated, branched or unbranched, wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and O—$C_{1-4}$-aliphatic residue, or a $C_{3-10}$-cycloaliphatic residue, saturated or unsaturated, branched or unbranched, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-10}$-cycloaliphatic residue is in each case optionally linked via a $C_{1-4}$-aliphatic group, which in turn is optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{11}$ and $R^{13}$, together with the carbon atom(s) joining them, form a $C_{3-10}$-cycloaliphatic residue or a 3 to 10 membered heterocycloaliphatic residue, in each case saturated or unsaturated and in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O) OH, wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-10}$-cycloaliphatic residue or the 3 to 10 membered heterocycloaliphatic residue is in each case optionally linked via a $C_{1-4}$-aliphatic group, which in turn is optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the remaining substituents $R^2$, $R^3$, $R^4$, $R^5$, $R^{10}$, $R^{11}$, $R^{12}$ and $R^{13}$ in each case have the meaning given above;

$R^6$ represents a $C_{3-10}$-cycloaliphatic residue or a 3 to 10 membered heterocycloaliphatic residue, in each case saturated or unsaturated and in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, $C_{3-6}$-cycloaliphatic residue and 3 to 7 membered heterocycloaliphatic residue, wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and O—$C_{1-4}$-aliphatic residue, and wherein the $C_{3-6}$-cycloaliphatic residue and the 3 to 7 membered heterocycloaliphatic residue is in each case optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, and wherein the $C_{3-10}$-cycloaliphatic residue or the 3 to 10 membered heterocycloaliphatic residue is in each case optionally linked via a $C_{1-4}$-aliphatic group, which in turn is optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue and C(=O)OH, or represents an aryl or heteroaryl, in each case unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue)$_2$, OH, O—$C_{1-4}$-aliphatic residue, $OCF_3$, SH, $SCF_3$, S—$C_{1-4}$-aliphatic residue, $CF_3$, CN, $C_{1-4}$-aliphatic residue, C(=O)OH, C(=O)$CH_3$, C(=O)$C_2H_5$, C(=O)$OCH_3$, C(=O)$OC_2H_5$, $C_{3-6}$-cycloaliphatic residue, 3 to 7 membered heterocycloaliphatic residue,

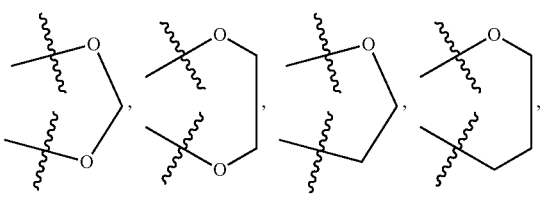

benzyl, phenyl, thienyl, pyridyl, furyl, thiazolyl and oxazolyl, wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and $O—C_{1-4}$-aliphatic residue, and wherein benzyl, phenyl, thienyl, pyridyl, furyl, thiazolyl and oxazolyl is in each case optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, $O—C_{1-4}$-aliphatic residue, $OCF_3$, $OCH_2CH_2OH$, $OCH_2OCH_3$, SH, $SCF_3$, $S—C_{1-4}$-aliphatic residue, $CF_3$, CN, $C_{1-4}$-aliphatic residue, $C(=O)OH$, $C(=O)CH_3$, $C(=O)C_2H_5$, $C(=O)OCH_3$ and $C(=O)OC_2H_5$, and wherein the $C_{3-6}$-cycloaliphatic residue and the 3 to 7 membered heterocycloaliphatic residue is in each case optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, $O—C_{1-4}$-aliphatic residue, $OCF_3$, SH, $SCF_3$, $S—C_{1-4}$-aliphatic residue, $CF_3$, CN, $C_{1-4}$-aliphatic residue and $C(=O)OH$, and wherein the aryl or the heteroaryl residue is in each case optionally linked via a $C_{1-4}$-aliphatic group, which in turn is optionally unsubstituted or mono- or polysubstituted with at least one substituent selected from the group consisting of F, Cl, Br, I, $NO_2$, $NH_2$, $NH(C_{1-4}$-aliphatic residue), $N(C_{1-4}$-aliphatic residue$)_2$, OH, $O—C_{1-4}$-aliphatic residue, $OCF_3$, SH, $SCF_3$, $S—C_{1-4}$-aliphatic residue, $CF_3$, CN and $C(=O)OH$, each $R^7$ independently of each other represents H, F; Cl; CN; $CF_3$; $CHF_2$; $CH_2F$; $OCF_3$; $OCHF_2$; $OCH_2F$; $SCF_3$; a $O—C_{1-4}$-aliphatic residue, a $C_{1-4}$-aliphatic residue or a $S(=O)_2—C_{1-4}$-aliphatic residue, wherein the $C_{1-4}$-aliphatic residue in each case is optionally unsubstituted or mono- or polysubstituted with at least one substituent selected from the group consisting of F, Cl, Br, I, OH, $OCF_3$, $CF_3$ and $O—C_{1-4}$-aliphatic residue, and $R^8$ represents H or $C_{1-4}$-aliphatic residue, wherein the $C_{1-4}$-aliphatic residue is optionally unsubstituted or mono- or polysubstituted with at least one substituent selected from the group consisting of F, Cl, Br, I, OH, $OCF_3$, $CF_3$ and $O—C_{1-4}$-aliphatic residue.

3. The compound according to claim 1, wherein
$A^1$ represents S; and
$A^2$ represents S, $S(=O)_2$ or $CR^{12}R^{13}$,
wherein $R^{12}$ and $R^{13}$ both represent H or both represent F.

4. The compound according to claim 1,
wherein
n denotes 1 and $A^3$ represents $CR^7$, $A^4$ represents $CR^7$, $A^5$ represents $CR^7$ and $A^6$ represents $CR^7$; or
n denotes 1 and $A^3$ represents N, $A^4$ represents $CR^7$, $A^5$ represents $CR^7$ and $A^6$ represents $CR^7$; or
n denotes 1 and $A^3$ represents $CR^7$, $A^4$ represents N, $A^5$ represents $CR^7$ and $A^6$ represents $CR^7$; or
n denotes 1 and $A^3$ represents $CR^7$, $A^4$ represents $CR^7$, $A^5$ represents N and $A^6$ represents $CR^7$; or
n denotes 1 and $A^3$ represents N, $A^4$ represents $CR^7$, $A^5$ represents N and $A^6$ represents $CR^7$; or
n denotes 1 and $A^3$ represents N, $A^4$ represents $CR^7$, $A^5$ represents $CR^7$ and $A^6$ represents N; or
n denotes 1 and $A^3$ represents $CR^7$, $A^4$ represents N, $A^5$ represents $CR^7$ and $A^6$ represents N; or
n denotes 1 and $A^3$ represents $CR^7$, $A^4$ represents N, $A^5$ represents N and $A^6$ represents $CR^7$; or
n denotes 1 and $A^3$ represents $CR^7$, $A^4$ represents $CR^7$, $A^5$ represents N and $A^6$ represents N; or
n denotes 0 and $A^3$ represents S, $A^4$ represents $CR^7$ and $A^5$ represents $CR^7$;
or
n denotes 0 and $A^3$ represents S, $A^4$ represents $CR^7$ and $A^5$ represents N;
or
n denotes 0 and $A^3$ represents 0, $A^4$ represents $CR^7$ and $A^5$ represents $CR^7$;
or
n denotes 0 and $A^3$ represents 0, $A^4$ represents $CR^7$ and $A^5$ represents N;
or
n denotes 0 and $A^3$ represents $CR^7$, $A^4$ represents $CR^7$ and $A^5$ represents S;
or
n denotes 0 and $A^3$ represents N, $A^4$ represents $CR^7$ and $A^5$ represents S;
or
n denotes 0 and $A^3$ represents $CR^7$, $A^4$ represents $CR^7$ and $A^5$ represents 0;
or
n denotes 0 and $A^3$ represents N, $A^4$ represents $CR^7$ and $A^5$ represents 0.

5. The compound according to claim 1, wherein
$R^1$ represents the partial structure (T1)

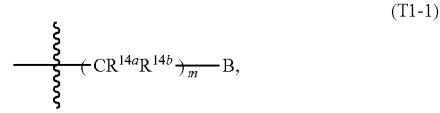

wherein
$R^{14a}$ and $R^{14b}$ each independently of the other represent H; F; Cl; Br; $CF_3$; CN; OH; $OCF_3$; $NH_2$; $C_{1-4}$-aliphatic residue, $O—C_{1-4}$-aliphatic residue, $NH(C_{1-4}$-aliphatic residue), $N(C_{1-4}$-aliphatic residue$)_2$, in each case saturated or unsaturated, branched or unbranched, unsubstituted or mono- or poly-substituted by one or more substituents each selected independently of one another from the group consisting of F, Cl, Br, I, $O—C_{1-4}$-aliphatic residue, OH and $OCF_3$;
or independently represent $C_{3-10}$-cycloaliphatic residue or 3 to 10 membered heterocycloaliphatic residue, in each case saturated or unsaturated, unsubstituted or mono- or poly-substituted by one or more substituents each selected independently of one another from the group consisting of F, Cl, Br, $C_{1-4}$-aliphatic residue, OH, $O—C_{1-4}$-aliphatic residue, $OCF_3$, $NH_2$, $NH(C_{1-4}$-aliphatic residue) and $N(C_{1-4}$-aliphatic residue$)_2$;
m represents 0, 1, 2 or 3;
Y represents O or $NR^{15}$,
wherein $R^{15}$ represents H or
$C_{1-4}$-aliphatic residue, saturated or unsaturated, branched or unbranched, unsubstituted or mono- or poly-substituted by one or more substituents each selected independently of one another from the group consisting of F, Cl, Br, $C_{1-4}$-aliphatic residue, OH, O—$C_{1-4}$-aliphatic residue, $OCF_3$, $NH_2$, NH($C_{1-4}$-aliphatic residue) and N($C_{1-4}$-aliphatic residue)$_2$; or $C_{3-10}$-cycloaliphatic residue, saturated or unsaturated, unsubstituted or mono- or poly-substituted by one or more substituents each selected independently of one another from the group consisting of F, Cl, Br, $C_{1-4}$-aliphatic residue, OH, O—$C_{1-4}$-aliphatic residue, $OCF_3$, $NH_2$, NH($C_{1-4}$-aliphatic residue) and N($C_{1-4}$-aliphatic residue)$_2$;

o represents 0 or 1,

B represents $C_{1-8}$-aliphatic residue, saturated or unsaturated, branched or unbranched, unsubstituted or mono- or poly-substituted by one or more substituents each selected independently of one another from the group consisting of F, Cl, Br, CN, OH, O—$C_{1-4}$-aliphatic residue, $OCF_3$, C(=O)OH, $CF_3$, $NH_2$, NH($C_{1-4}$-aliphatic residue) and N($C_{1-4}$-aliphatic residue)$_2$;

or $C_{3-10}$-cycloaliphatic residue or 3 to 10 membered heterocycloaliphatic residue, in each case saturated or unsaturated, unsubstituted or mono- or poly-substituted by one or more substituents each selected independently of one another from the group consisting of F, Cl, Br, CN, OH, O—$C_{1-4}$-aliphatic residue, $OCF_3$, $C_{1-4}$-aliphatic residue, C(=O)—OH, $CF_3$, $NH_2$, NH($C_{1-4}$-aliphatic residue), N($C_{1-4}$-aliphatic residue)$_2$ and $SCF_3$;

or aryl or heteroaryl, in each case unsubstituted or mono- or poly-substituted by one or more substituents each selected independently of one another from the group consisting of F, Cl, Br, $NO_2$, CN, OH, O—$C_{1-4}$-aliphatic residue, $OCF_3$, $C_{1-4}$-aliphatic residue, C(=O) OH, $CF_3$, $NH_2$, NH($C_{1-4}$-aliphatic residue), N($C_{1-4}$-aliphatic residue)$_2$, S—$C_{1-4}$-aliphatic residue, $SCF_3$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, $NO_2$, CN, OH, O—$C_{1-4}$-aliphatic residue, $OCF_3$, $C_{1-4}$-aliphatic residue, C(=O)—OH, $CF_3$, $NH_2$, NH($C_{1-4}$-aliphatic residue), N($C_{1-4}$-aliphatic residue)$_2$, S—$C_{1-4}$-aliphatic residue and $SCF_3$.

6. The compound according to claim 5, wherein $R^{14a}$ and $R^{14b}$ each independently of the other represents H; F; Cl; $CH_3$; $CH_2CH_3$; $(CH_2)_2CH_3$; $CH(CH_3)_2$; $(CH_2)_3CH_3$; $CH(CH)_3CH_2CH_3$; $C(CH_3)_3$; OH; $OCH_3$; $OCH_2CH_3$; $O(CH_2)_2OCH_3$ or $O(CH_2)_2OH$;

m represents 0, 1 or 2 and o represents 0 and

B represents $CH_3$; $CH_2CH_3$; $(CH_2)_2CH_3$; $CH(CH_3)_2$; $(CH_2)_3CH_3$; $CH(CH_3)CH_2CH_3$; $C(CH_3)_3$; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl or thienyl, in each case unsubstituted or mono-, di- or tri-substituted by one, two or three substituents each selected independently of one another from the group consisting of F, Cl, CN, OH, O—$C_{1-4}$-aliphatic residue, $OCF_3$, $C_{1-4}$-aliphatic residue, $CF_3$, $NH_2$, NH($C_{1-4}$-aliphatic residue) and N($C_{1-4}$-aliphatic residue)$_2$.

7. The compound according to claim 1, wherein $R^2$, $R^3$, $R^4$, $R^5$, $R^{10}$, $R^{11}$, $R^{12}$ and $R^{13}$ each independently of the others represents H; F; Cl; $CF_3$; CN; OH; $OCF_3$; $SCF_3$; $CH_3$; $CH_2CH_3$; $(CH_2)_2CH_3$; $CH(CH_3)_2$; $(CH_2)_3CH_3$; $CH(CH)_3CH_2CH_3$; $C(CH_3)_3$; $OCH_3$; $OCH_2CH_3$; $O(CH_2)_2OCH_3$; $O(CH_2)_2OH$; $SCH_3$; $SCH_2CH_3$; cyclopropyl; cyclobutyl; cyclopentyl; cyclohexyl;

or $R^2$ and $R^3$ or $R^4$ and $R^5$ or $R^{10}$ and $R^{11}$ or $R^{12}$ and $R^{13}$ or $R^2$ and $R^{11}$ or $R^2$ and $R^4$ or $R^2$ and $R^{13}$ or $R^4$ and $R^{13}$ or $R^4$ and $R^{11}$ or $R^{11}$ and $R^{13}$, together with the carbon atom(s) joining them, form a cyclopropyl, cyclobutyl, cyclopentyl or cyclohexyl, in each case unsubstituted;

wherein the remaining substituents $R^2$, $R^3$, $R^4$, $R^5$, $R^{10}$, $R^{11}$, $R^{12}$ and $R^{13}$ in each case have the meaning given above.

8. The compound according to claim 1, wherein each $R^7$ represents H, F; Cl; CN; $CF_3$; $CHF_2$; $CH_2F$; $OCF_3$; $OCHF_2$; $OCH_2F$; $SCF_3$; $CH_3$; $CH_2CH_3$; $CH_2CH_2CH_3$; $CH(CH_3)_2$; $CH_2CH_2CH_2CH_3$; $CH(CH)_3CH_2CH_3$; $CH_2CH(CH_3)_2$; $C(CH_3)_3$; $OCH_3$; $OCH_2CH_3$; O$(CH_2)_2OCH_3$; $O(CH_2)_2OH$; S(=O)$_2CH_3$S(=O)$_2$$CH_2CH_3$S(=O)$_2$CH($CH_3$)$_2$ or S(=O)$_2CH_2CH_2CH_3$;

and $R^8$ represents H or $CH_3$ or $CH_2CH_3$ or $CH(CH_3)_2$.

9. The compound according to claim 1, wherein $R^6$ represents a $C_{3-10}$-cycloaliphatic residue or a 3 to 10 membered heterocycloaliphatic residue, in each case saturated or unsaturated, unsubstituted or mono- or poly-substituted by one or more substituents each selected independently of one another from the group consisting of F, Cl, Br, I, $NO_2$, CN, OH, O—$C_{1-4}$-aliphatic residue, $OCF_3$, $C_{1-4}$-aliphatic residue, $CF_3$, SH, S—$C_{1-4}$-aliphatic residue and $SCF_3$;

or an aryl or a heteroaryl, in each case unsubstituted or mono- or poly-substituted by one or more substituents each selected independently of one another from the group consisting of F, Cl, Br, I, $NO_2$, CN, OH, O—$C_{1-4}$-aliphatic residue, $OCF_3$, $C_{1-4}$-aliphatic residue, $CF_3$, $NH_2$, NH($C_{1-4}$-aliphatic residue), N($C_{1-4}$-aliphatic residue)$_2$, SH, S—$C_{1-4}$-aliphatic residue and $SCF_3$.

10. The compound according to claim 1, wherein $R^6$ represents phenyl, pyridyl or thienyl, in each case unsubstituted or mono- or poly-substituted by one or more substituents each selected independently of one another from the group consisting of F, Cl, Br, CN, OH, O—$C_{1-4}$-aliphatic residue, $OCF_3$, $C_{1-4}$-aliphatic residue, $CF_3$ and $SCF_3$.

11. A compound according to claim 1, wherein $A^1$ represents S; and $A^2$ represents S, S(=O)$_2$ or $CR^{12}R^{13}$, wherein $R^{12}$ and $R^{13}$ both represent H or both represent F; and $R^1$ represents the partial structure (T1-1)

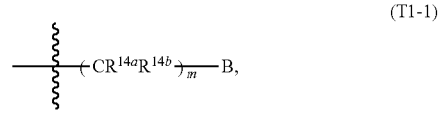

(T1-1)

wherein $R^{14a}$ and $R^{14b}$ each independently of the other represents H; F; Cl; $CH_3$; $CH_2CH_3$; $(CH_2)_2CH_3$; $CH(CH_3)_2$; $(CH_2)_3CH_3$; $CH(CH)_3CH_2CH_3$; $C(CH_3)_3$; OH; $OCH_3$; $OCH_2CH_3$; $O(CH_2)_2OCH_3$; or $O(CH_2)_2OH$;

m represents 0, 1 or 2 and

B represents phenyl or naphthyl or pyridyl or thienyl, in each case unsubstituted or mono- or di- or tri-substituted by one, two or three substituents each selected independently of one another from the group consisting of F, Cl, CN, OH, O-$_{1-4}$-aliphatic residue, OCF$_3$, C$_{1-4}$-aliphatic residue, C(=O)—OH, CF$_3$, NH$_2$, NH(C$_{1-4}$-aliphatic residue) and N(C$_{1-4}$-aliphatic residue)$_2$;

R$^2$, R$^3$, R$^4$, R$^5$, R$^{10}$, R$^{11}$, R$^{12}$ and R$^{13}$ each independently of the others represent H; F; Cl; Br; I; NO$_2$; CF$_3$; CN; OH; OCF$_3$; SH; SCF$_3$; CH$_3$; CH$_2$CH$_3$; CH$_2$CH$_2$CH$_3$; CH(CH$_3$)$_2$; CH$_2$CH$_2$CH$_2$CH$_3$; CH(CH)$_3$CH$_2$CH$_3$; CH$_2$CH(CH$_3$)$_2$; C(CH$_3$)$_3$; OCH$_3$; OCH$_2$CH$_3$; O(CH$_2$)$_2$OCH$_3$; O(CH$_2$)$_2$OH; SCH$_3$; SCH$_2$CH$_3$; cyclopropyl; cyclobutyl; cyclopentyl; cyclohexyl;

or R$^2$ and R$^3$ or R$^4$ and R$^5$ or R$^{10}$ and R$^{11}$ or R$^{12}$ and R$^{13}$ or R$^2$ and R$^{11}$ or R$^2$ and R$^4$ or R$^2$ and R$^{13}$ or R$^4$ and R$^{13}$ or R$^4$ and R$^{11}$ or R$^{11}$ and R$^{13}$, together with the carbon atom(s) joining them, form a cyclopropyl, cyclobutyl, cyclopentyl or cyclohexyl, in each case unsubstituted; wherein the remaining substituents R$^2$, R$^3$, R$^4$, R$^5$, R$^{10}$, R$^{11}$, R$^{12}$ and R$^{13}$ in each case have the meaning given above;

R$^6$ represents phenyl, in each case unsubstituted or mono- or poly-substituted by one or more substituents each selected independently of one another from the group consisting of F, Cl, Br, I, CN, OH, OCH$_3$, OCH$_2$CH$_3$, OCF$_3$, CH$_3$, CH$_2$CH$_3$, CH(CH$_3$)$_2$ and CF$_3$;

each R$^7$ represents H, F; Cl; CN; CF$_3$; CHF$_2$; CH$_2$F; OCF$_3$; OCHF$_2$; OCH$_2$F; SCF$_3$; CH$_3$; CH$_2$CH$_3$; CH$_2$CH$_2$CH$_3$; CH(CH$_3$)$_2$; CH$_2$CH$_2$CH$_2$CH$_3$; CH(CH)$_3$CH$_2$CH$_3$; CH$_2$CH(CH$_3$)$_2$; C(CH$_3$)$_3$; OCH$_3$; OCH$_2$CH$_3$; O(CH$_2$)$_2$OCH$_3$; O(CH$_2$)$_2$OH; S(=O)$_2$CH$_3$S(=O)$_2$CH$_2$CH$_3$, S(=O)$_2$CH(CH$_3$)$_2$ or S(=O)$_2$CH$_2$CH$_2$CH$_3$;

and R$^8$ represents H or CH$_3$ or CH$_2$CH$_3$ or CH(CH$_3$)$_2$.

12. The compound according to claim 1, wherein the compound is selected from the group consisting of:

1  2-[[3,3-Difluoro-3-(4-fluorophenyl)-propyl]sulfanyl]-N-(3-methyl-butyl)-benzamide;
2  N-(3,3-Dimethyl-butyl)-2-[3-(4-fluorophenyl)-propylsulfanyl]-benzamide;
3  3-[[3,3-Difluoro-3-(4-fluorophenyl)-propyl]sulfanyl]-N-(3-methyl-butyl)-pyridine-2-carboxylic acid amide;
4  3-[2-(Benzenesulfonyl)-ethylsulfanyl]-N-(thiophen-2-yl-methyl)-pyridine-2-carboxylic acid amide;
5  4-[[3,3-Difluoro-3-(4-fluorophenyl)-propyl]sulfanyl]-N-(3-methyl-butyl)-pyridine-3-carboxylic acid amide;
6  4-[[3,3-Difluoro-3-(4-fluorophenyl)-propyl]sulfanyl]-N-[(4-fluorophenyl)-methyl]-pyridine-3-carboxylic acid amide;
7  3-[[3,3-Difluoro-3-(4-fluorophenyl)-propyl]sulfanyl]-N-(3-methyl-butyl)-pyridine-4-carboxylic acid amide;
8  3-[2-(Benzenesulfonyl)-ethylsulfanyl]-N-(thiophen-2-yl-methyl)-pyridine-4-carboxylic acid amide;
9  3-[[3,3-Difluoro-3-(4-fluorophenyl)-propyl]sulfanyl]-N-(3-methyl-butyl)-pyrazine-2-carboxylic acid amide;
10  4-[[3,3-Difluoro-3-(4-fluorophenyl)-propyl]sulfanyl]-N-(3-methyl-butyl)-pyrimidine-5-carboxylic acid amide;
11  4-[[3,3-Difluoro-3-(4-fluorophenyl)-propyl]sulfanyl]-N-[(4-fluorophenyl)-methyl]-pyrimidine-5-carboxylic acid amide;
12  3-[[3,3-Difluoro-3-(4-fluorophenyl)-propyl]sulfanyl]-N-(3-methyl-butyl)-pyridazine-4-carboxylic acid amide;
13  3-[[3,3-Difluoro-3-(4-fluorophenyl)-propyl]sulfanyl]-N-[(4-fluorophenyl)-methyl]-pyridazine-4-carboxylic acid amide;
14  4-[[3,3-Difluoro-3-(4-fluorophenyl)-propyl]sulfanyl]-N-[(4-fluorophenyl)-methyl]-thiazole-5-carboxylic acid amide; and
15  4-[[3,3-Difluoro-3-(4-fluorophenyl)-propyl]sulfanyl]-N-[(4-fluorophenyl)-methyl]-2-methyl-thiazole-5-carboxylic acid amide;

in the form of a free compound, a solvate and and/or a physiologically acceptable salt.

13. A pharmaceutical composition comprising at least one compound according to claim 1 in the form of an individual single stereoisomer or a mixture of the stereoisomers in any mixing ratio, in the form of a free compound and/or in the form of a solvate and and/or a physiologically acceptable salt, and optionally at least one pharmaceutically acceptable auxiliary and/or optionally at least one further active ingredient.

14. A method for treatment of disorders and/or diseases which are mediated, at least in part, by KCNQ2/3 K$^+$ channels in a patient in need thereof, said method comprising administering to said patient an effective amount therefor of a compound according to claim 1.

15. The method according to claim 14, wherein the disorders and/or diseases are selected from the group consisting of pain, acute pain, chronic pain, neuropathic pain, muscular pain, visceral pain, inflammatory pain, epilepsy, urinary incontinence, anxiety, dependency, mania, bipolar disorders, migraine, cognitive diseases and dystonia-associated dyskinesias.

16. A method for treatment of disorders and/or diseases selected from the group consisting of pain, acute pain, chronic pain, neuropathic pain, muscular pain, visceral pain, inflammatory pain, epilepsy, urinary incontinence, anxiety, dependency, mania, bipolar disorders, migraine, cognitive diseases and dystonia-associated dyskinesias in a patient in need thereof, said method comprising administering to said patient an effective amount therefor of a compound according to claim 1.

* * * * *